(12) United States Patent
Thirumalai Rajan et al.

(10) Patent No.: US 9,273,030 B2
(45) Date of Patent: Mar. 1, 2016

(54) PROCESS FOR THE PREPARATION OF BENZIMIDAZOLE DERIVATIVES AND SALTS THEREOF

(71) Applicant: MSN Laboratories Private Limited, Telangana (IN)

(72) Inventors: Srinivasan Thirumalai Rajan, Hyderabad (IN); Sajja Eswaraiah, Hyderabad (IN); Suraparaju Raghuram, Hyderabad (IN)

(73) Assignee: MSN Laboratories Private Limited, Rudraram (Village), Patancheru (Mandal), Medak District, Telangana (IN)

( * ) Notice: Subject to any disclaimer, the term of this patent is extended or adjusted under 35 U.S.C. 154(b) by 0 days.

(21) Appl. No.: 14/394,409

(22) PCT Filed: Apr. 1, 2013

(86) PCT No.: PCT/IN2013/000213
§ 371 (c)(1),
(2) Date: Oct. 14, 2014

(87) PCT Pub. No.: WO2013/150545
PCT Pub. Date: Oct. 10, 2013

(65) Prior Publication Data
US 2015/0087842 A1    Mar. 26, 2015

(30) Foreign Application Priority Data

Apr. 2, 2012 (IN) .............................. 1303/CHE/2012
Sep. 4, 2012 (IN) .............................. 3639/CHE/2012

(51) Int. Cl.
C07D 401/12    (2006.01)
C07D 213/81    (2006.01)
C07D 213/75    (2006.01)

(52) U.S. Cl.
CPC ............ *C07D 401/12* (2013.01); *C07D 213/75* (2013.01); *C07D 213/81* (2013.01); *C07B 2200/13* (2013.01); *Y10T 428/2982* (2013.01)

(58) Field of Classification Search
CPC .................................................... C07D 401/12
USPC ..................................................... 546/273.4
See application file for complete search history.

(56) References Cited

U.S. PATENT DOCUMENTS

| | | | |
|---|---|---|---|
| 9,006,448 B2 | 4/2015 | Reddy et al. | |
| 2005/0095293 A1 | 5/2005 | Brauns et al. | |
| 2005/0234104 A1 | 10/2005 | Schmid et al. | |
| 2007/0185173 A1 | 8/2007 | Zerban et al. | |
| 2010/0210845 A1 | 8/2010 | Zerban et al. | |

FOREIGN PATENT DOCUMENTS

| | | |
|---|---|---|
| CN | 102050814 | 5/2011 |
| WO | WO 98/37075 | 8/1998 |
| WO | WO 03/074056 A1 | 9/2003 |
| WO | WO 2005/028468 A1 | 3/2005 |
| WO | WO 2006/000353 A1 | 1/2006 |
| WO | WO 2006/114415 A2 | 11/2006 |
| WO | WO 2007/071742 A1 | 6/2007 |
| WO | WO 2008/043759 A1 | 4/2008 |
| WO | WO 2008/095928 A1 | 8/2008 |
| WO | WO 2009/111997 A1 | 12/2009 |
| WO | WO 2009/153214 A1 | 12/2009 |
| WO | WO 2009/153215 A1 | 12/2009 |
| WO | WO 2010/045900 A1 | 4/2010 |
| WO | WO 2011/061080 A1 | 5/2011 |
| WO | WO 2011/110478 A1 | 9/2011 |
| WO | WO 2011/110876 A1 | 9/2011 |
| WO | WO 2012/004396 A2 | 1/2012 |
| WO | WO 2012/004397 A1 | 1/2012 |
| WO | WO 2012/027543 A1 | 3/2012 |
| WO | WO 2012/044595 A1 | 4/2012 |

OTHER PUBLICATIONS

International Search Report for International Application No. PCT/IN2011/00836, "Process for the Preparation of Benzimidazole Derivatives and Its Salts" Date of mailing: Jul. 12, 2012.
(Continued)

*Primary Examiner* — Patricia L Morris
(74) *Attorney, Agent, or Firm* — Hamilton, Brook, Smith & Reynolds, P.C.

(57) ABSTRACT

Provided are novel salts of benzimidazole derivatives, preferably salts of benzimidazole derivatives which are useful intermediates in the synthesis of pure 1-methyl-2-[N-[4-(N-n-hexyloxycarbonylamidino)phenyl]aminomethyl]benzimidazol-5-yl-carboxylicacid-N-(2-pyridyl)-N-(2-ethoxycarbonylethyl)amide and its salts.

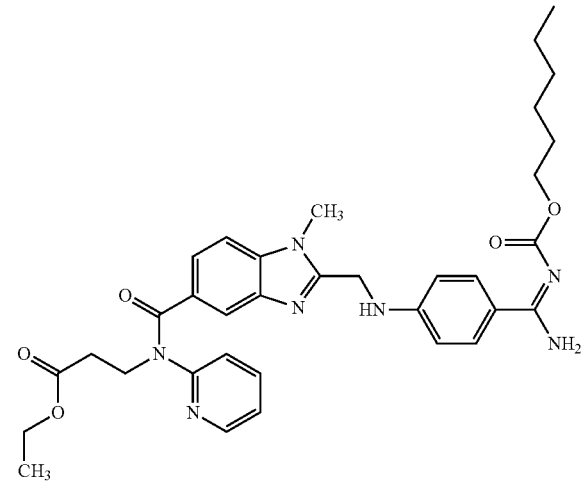

Formula-1

15 Claims, 9 Drawing Sheets

(56) References Cited

OTHER PUBLICATIONS

Written Opinion of the International Searching Authority for International Application No. PCT/IN2011/00836, "Process for the Preparation of Benzimidazole Derivatives and Its Salts", Date of mailing: Jul. 12, 2012.
Notification Concerning Transmittal of International Preliminary Report on Patentability for International Application No. PCT/IN2011/00836, "Process for the Preparation of Benzimidazole Derivatives and Its Salts" Date of Issuance: Jun. 12, 2013.

Hauel, N.H., et al., "Structure-Based Design of Novel Potent Nonpeptide Thrombin Inhibitors", *J. Med. Chem.*, 45: 1757-1766 (2002).
International Search Report for International Application No. PCT/IN2013/000213 , "Process for the Preparation of Benzimidazole Derivatives and Salts Thereof", date of mailing: Oct. 31, 2013.
International Preliminary Report on Patentability and Written Opinion of the International Searching Authority for International Application No. PCT/IN2013/000213 , "Process for the Preparation of Benzimidazole Derivatives and Salts Thereof", date of issuance of report: Oct. 7, 2014.

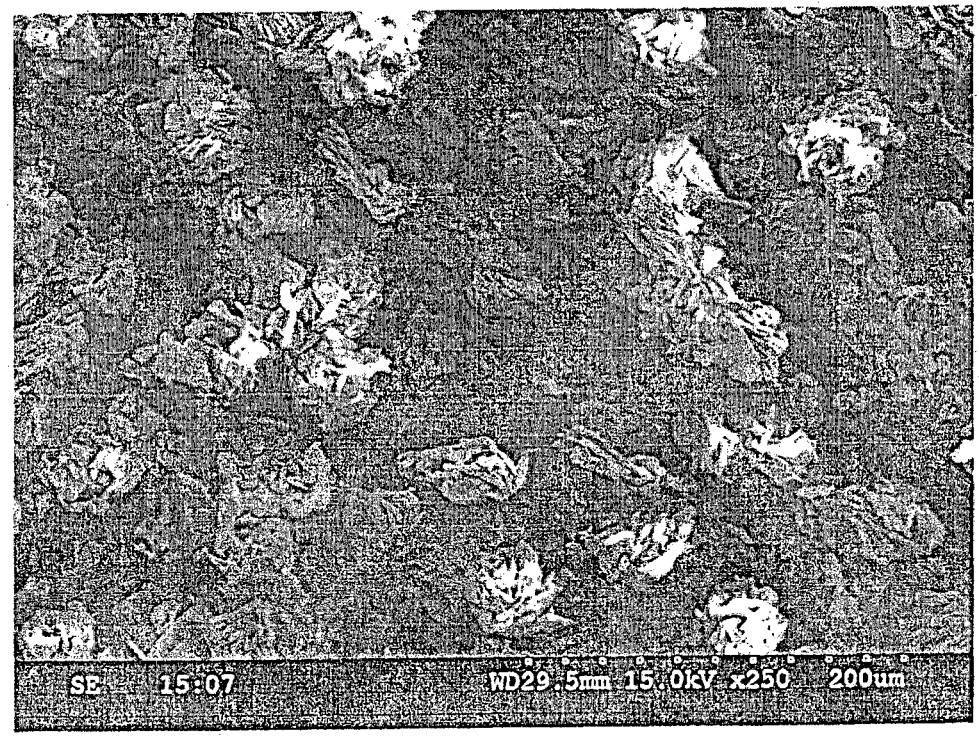
Figure-11

PROCESS FOR THE PREPARATION OF BENZIMIDAZOLE DERIVATIVES AND SALTS THEREOF

RELATED APPLICATIONS

This application is the U.S. National Stage of International Application No. PCT/IN2013/000213, filed Apr. 1, 2013, which designates the U.S., published in English, and claims priority under 35 U.S.C. 119 or 365(c) to Indian Application No. 1303/CHE/2012, filed Apr. 2, 2012 and Indian Application No. 3639/CHE/2012 filed on Sep. 5, 2012, which are incorporated herein by reference.

FIELD OF INVENTION

The present invention relates to novel salts of benzimidazole derivatives, preferably mesylate salt of benzimidazole derivatives which are useful intermediates in the synthesis of pure 1-methyl-2-[N-[4-(N-n-hexyloxycarbonylamidino) phenyl]aminomethyl]benzimidazol-5-yl-carboxylicacid-N-(2-pyridyl)-N-(2-ethoxycarbonylethyl)amide represented by the structural formula-1 and its pharmaceutically acceptable salts, preferably mesylate salt compound of formula-1a.

Formula-1

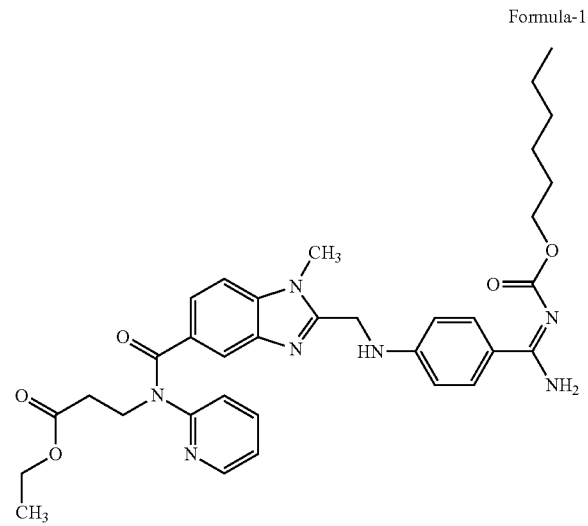 [SMILES: CCCCCCOC(=O)/N=C(/N)c1ccc(NCc2nc3cc(C(=O)N(CCC(=O)OCC)c4ccccn4)ccc3n2C)cc1]

The present invention also provides camphor sulfonate salt of 1-methyl-2-[N-[4-(N-n-hexyloxycarbonylamidino)phenyl]aminomethyl]benzimidazol-5-yl-carboxylicacid-N-(2-pyridyl)-N-(2-ethoxycarbonylethyl)amide compound of formula-1 and their polymorphs.

Further, the present invention also provides novel crystalline forms of 1-methyl-2-[N-[4-(N-n-hexyloxycarbonylamidino)phenyl]aminomethyl]benzimidazol-5-yl-carboxylicacid-N-(2-pyridyl)-N-(2-ethoxycarbonylethyl)amide salts, preferably oxalate and fumarate salts.

The present invention also provides an improved process for the preparation of ethyl 3-(3-amino-4-(methylamino)-N-(pyridin-2-yl)benzamido)propanoate compound of formula-7, which is a key intermediate in the synthesis of benzimidazole derivatives such as 1-methyl-2-[N-[4-(N-n-hexyloxycarbonylamidino)phenyl]aminomethyl] benzimidazol-5-yl-carboxylicacid-N-(2-pyridyl)-N-(2-ethoxycarbonylethyl)amide mesylate represented by structural formula-1a.

BACKGROUND OF THE INVENTION 1-methyl-2-[N-[4-(N-n-hexyloxycarbonylamidino)phenyl]aminomethyl]benzimidazole-5-yl-carboxylicacid-N-(2-pyridyl)-N-(2-ethoxycarbonylethyl)amide is commonly known as Dabigatran etexilate. Dabigatran is an anticoagulant from the class of the direct thrombin inhibitors developed by Boehringer Ingelheim and is used for the treatment of thrombosis, cardiovascular diseases, and the like. Dabigatran etexilate mesylate was approved in both US and Europe and commercially available under the brand name Pradaxa.

Dabigatran etexilate and process for its preparation was first disclosed in WO 98/37075. The disclosed process involves the reaction of ethyl 3-(3-amino-4-(methylamino)-N-(pyridin-2-yl)benzamido)propanoate with 2-(4-cyanophenylamino) acetic acid in the presence of N,N-carbonyldiimidazole in tetrahydrofuran to provide ethyl 3-(2-((4-cyanophenylamino)methyl)-1-methyl-N-(pyridin-2-yl)-1H-benzo[d]imidazole-5-carboxamido)propanoate, which is further converted into 1-methyl-2-[N-[4-amidinophenyl] aminomethyl]benzimidazol-5-ylcarboxylicacid-N-(2-pyridyl)-N-(2-ethoxycarbonylethyl)amide hydrochloride by reacting with ammonium carbonate in ethanol, followed by treating with ethanolic hydrochloric acid. The obtained compound was reacted with n-hexyl chloroformate in presence of potassium carbonate in tetrahydrofuran/water provides Dabigatran etexilate and further conversion into its mesylate salt was not disclosed. The purity of Dabigatran etexilate prepared as per the disclosed process is not satisfactory, and also the said process involves chromatographic purification which is expensive and difficult to implement in the large scale. Hence the said process is not suitable for commercial scale up.

Moreover, the said process proceeds through the 1-methyl-2-[N-[4-amidinophenyl]aminomethyl]benzimidazol-5-yl-carboxylicacid-N-(2-pyridyl)-N-(2-ethoxycarbonylethyl) amide hydrochloride (herein after referred as "Dabigatran hydrochloride"), which degrades to form impurities and resulting in the formation of Dabigatran etexilate with low purity. In view of intrinsic fragility of Dabigatran hydrochloride, there is a need in the art to develop a novel salt form of 1-methyl-2-[N-[4-amidinophenyl]aminomethyl]benzimidazol-5-ylcarboxylicacid-N-(2-pyridyl)-N-(2-ethoxycarbonyl ethyl)amide, which enhances the purity of the final compound.

The prior reported processes disclosed in WO2012004396 and WO2008095928 A1 involves the usage of inorganic salts like hydrochloride and hydrobromide salts of ethyl 3-(2-((4-cyanophenylamino)methyl)-1-methyl-N-(pyridin-2-yl)-1H-benzo[d]imidazole-5-carboxamido) propanoate (herein after referred as "cyano intermediate") and ethyl 3-(2-((4-carbamimidoyl phenylamino)methyl)-1-methyl-N-(pyridin-2-yl)-1H-benzo[d]imidazole-5-carboxamido) propanoate (herein after referred as "amidino intermediate"). The inorganic acid addition salts are less stable when compared to the organic acid addition salts and also the process for the preparation of organic acid addition salts is very much easy when compared to inorganic acid addition salt. Inorganic acid addition salts of amidine intermediate seem to be hygroscopic in nature. Therefore, organic acid addition salts are always preferable to synthesize stable salts which in-turn enhances the purity of the final compound.

The oxalate salt of cyano intermediate was disclosed in WO2009111997. However as on date, there is no other organic acid addition salts of cyano intermediate were reported in the prior art for preparing pure Dabigatran etexilate. Henceforth, there is a need to develop a novel organic acid addition salt of cyano intermediate compound which is very much efficient when compared to its corresponding oxalate salt and that result in the formation of final compound with high purity and yield.

The process disclosed in WO 98/37075 also involves the reduction of ethyl 3-(4-(methylamino)-3-nitro-N-(pyridin-2-yl)benzamido)propanoate (herein after referred as "nitro compound") using Pd—C in a mixture of dichloromethane and methanol under hydrogen pressure to provide ethyl 3-(3-amino-4-(methylamino)-N-(pyridin-2-yl)benzamido)propanoate (herein after referred as "diamine compound").

The reduction of nitro compound through catalytic hydrogenation in the presence of tertiary amine under hydrogen pressure was also disclosed in WO2009153214; and in presence of inorganic base under hydrogen pressure was also disclosed in WO2012004397.

However, most of the prior art processes proceed through catalytic hydrogenation which involves the pressure reactions. Handlings of these pressure reactions are not suitable for the large scale process. Therefore, there is a significant need in the art to provide a simple reduction process which avoids the difficulties associated with catalytic hydrogenation.

JMC, 2002, 45(9), 1757-1766 disclosed a process for the preparation of ethyl 3-(3-amino-4-(methylamino)-N-(pyridin-2-yl)benzamido)propanoate starting from 4-(methylamino)-3-nitrobenzoic acid. The disclosed process involves the conversion of 4-(methylamino)-3-nitrobenzoic acid into its acid chloride using thionyl chloride and the obtained compound was reacted with ethyl 3-(pyridin-2-ylamino)propanoate to provide nitro compound, followed by catalytic reduction using Pd—C to provide diamine compound.

However, particularly in large scale synthesis the reduction reaction occasionally stops due to catalyst poisoning which leads to incomplete reaction and requires additional catalyst to complete the reaction. Moreover the sulfur impurities which are present in nitro compound formed due to the reaction with thionyl chloride in the previous stages of the synthesis of diamine compound are strongly influence the reaction time, quality and catalyst consumption in the manufacturing process.

Surprisingly, the problem associated with the catalytic hydrogenation and catalyst poisoning is solved by the present invention by adopting a suitable reducing agent such as Fe-acetic acid and Fe-hydrochloric acid.

The crystalline forms-I, II, V and VI of Dabigatran etexilate oxalate were disclosed in WO2008043759 and WO2011110876.

The crystalline forms-III, IV and V of Dabigatran etexilate fumarate were disclosed in WO2008043759 and WO2011110876.

Various different salts for Dabigatran etexilate and their polymorphs were reported in WO98/37075, WO03074056, WO2005028468, WO2006114415, WO2008043759, WO2011110876, WO2012027543 and WO2012044595.

The process for the preparation of crystalline form-I of Dabigatran etexilate mesylate was described in WO2005028468 and WO2012027543.

SUMMARY OF THE INVENTION

The first aspect of the present invention is to provide a process for the preparation of ethyl 3-(3-amino-4-(methylamino)-N-(pyridin-2-yl)benzamido)propanoate compound of formula-7, comprising of reducing ethyl 3-(4-(methylamino)-3-nitro-N-(pyridin-2-yl)benzamido) propanoate compound of formula-6 with Fe-acetic acid (or) Fe-hydrochloric acid in a suitable solvent.

The second aspect of the present invention is to provide ethyl 3-(2-((4-cyano phenyl amino)methyl)-1-methyl-N-(pyridin-2-yl)-1H-benzo[d]imidazole-5-carboxamido) propanoate mesylate compound of formula-10 and process for its preparation.

The third aspect of the present invention is to provide ethyl 3-(2-((4-carbamimidoyl phenylamino)methyl)-1-methyl-N-(pyridin-2-yl)-1H-benzo[d]imidazole-5-carboxamido) propanoate mesylate compound of formula-11 and process for its preparation.

The fourth aspect of the present invention is to provide a process for the purification of ethyl 3-(2-((4-carbamimidoylphenylamino)methyl)-1-methyl-N-(pyridin-2-yl)-1H-benzo[d]imidazole-5-carboxamido)propanoate mesylate compound of formula-11.

The fifth aspect of the present invention is to provide a process for the preparation of 1-methyl-2-[N-[4-(N-n-hexyloxycarbonylamidino)phenyl]aminomethyl]benzimidazol-5-yl-carboxylic acid-N-(2-pyridyl)-N-(2-ethoxycarbonylethyl)amide compound of formula-1 from ethyl 3-(2-((4-carbamimidoylphenylamino)methyl)-1-methyl-N-(pyridin-2-yl)-1H-benzo[d]imidazole-5-carboxamido) propanoate mesylate compound of formula-11.

The sixth aspect of the present invention is to provide a process for the preparation of 1-methyl-2-[N-[4-(N-n-hexyloxycarbonylamidino)phenyl]aminomethyl]benzimidazol-5-yl-carboxylicacid-N-(2-pyridyl)-N-(2-ethoxy carbonylethyl)amide compound of formula-1.

The seventh aspect of the present invention is to provide (−)-camphor sulfonate salt of Dabigatran etexilate compound of formula-1 and process for its preparation.

The eighth aspect of the present invention relates to crystalline form-M of Dabigatran etexilate (−)-camphor sulfonate and process for its preparation.

The ninth aspect of the present invention relates to amorphous form of Dabigatran etexilate (−)-camphor sulfonate and process for its preparation.

The tenth aspect of the present invention relates to novel crystalline form-S of Dabigatran etexilate oxalate and process for its preparation.

The eleventh aspect of the present invention relates to novel crystalline form-N of Dabigatran etexilate fumarate and its process for the preparation.

The twelfth aspect of the present invention is to provide a process for the preparation of crystalline form-I of Dabigatran etexilate mesylate compound of formula-1a from acetonitrile solvent.

Advantages of the Present Invention

Avoids the usage of hydrogenation and pressure reactions.
Avoids costly metal catalysts like Pd—C.
Provides novel salts of cyano intermediate and amidino intermediate which will enhance the purity of final compound i.e. Dabigatran etexilate and its salts.
Provides novel camphor sulfonate salt of Dabigatran etexilate.
Provides novel polymorphs for Dabigatran etexilate salts such as oxalate, fumarate and camphor sulfonate salt.
Provides simple, safer, environmental friendly and cost-effective process.

(pyridin-2-yl)-1H-benzo[d]imidazole-5-carboxamido) propanoate mesylate compound of formula-10.

Figure 2:
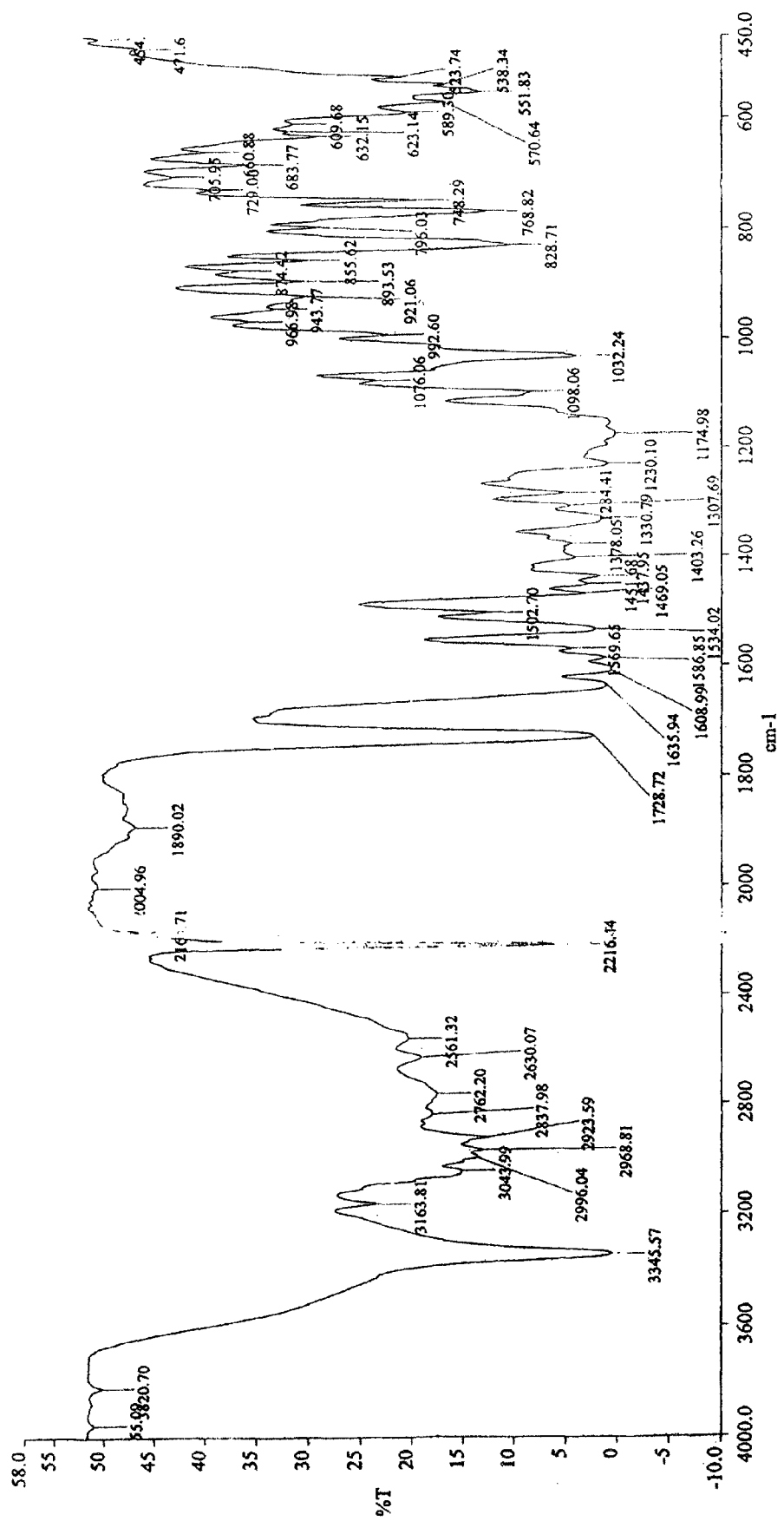

FIG. 2: Illustrates the IR spectrum of crystalline form-M of ethyl 3-(2-((4-cyano phenylamino)methyl)-1-methyl-N-(pyridin-2-yl)-1H-benzo[d]imidazole-5-carboxamido) propanoate mesylate compound of formula-10.

Figure 3:
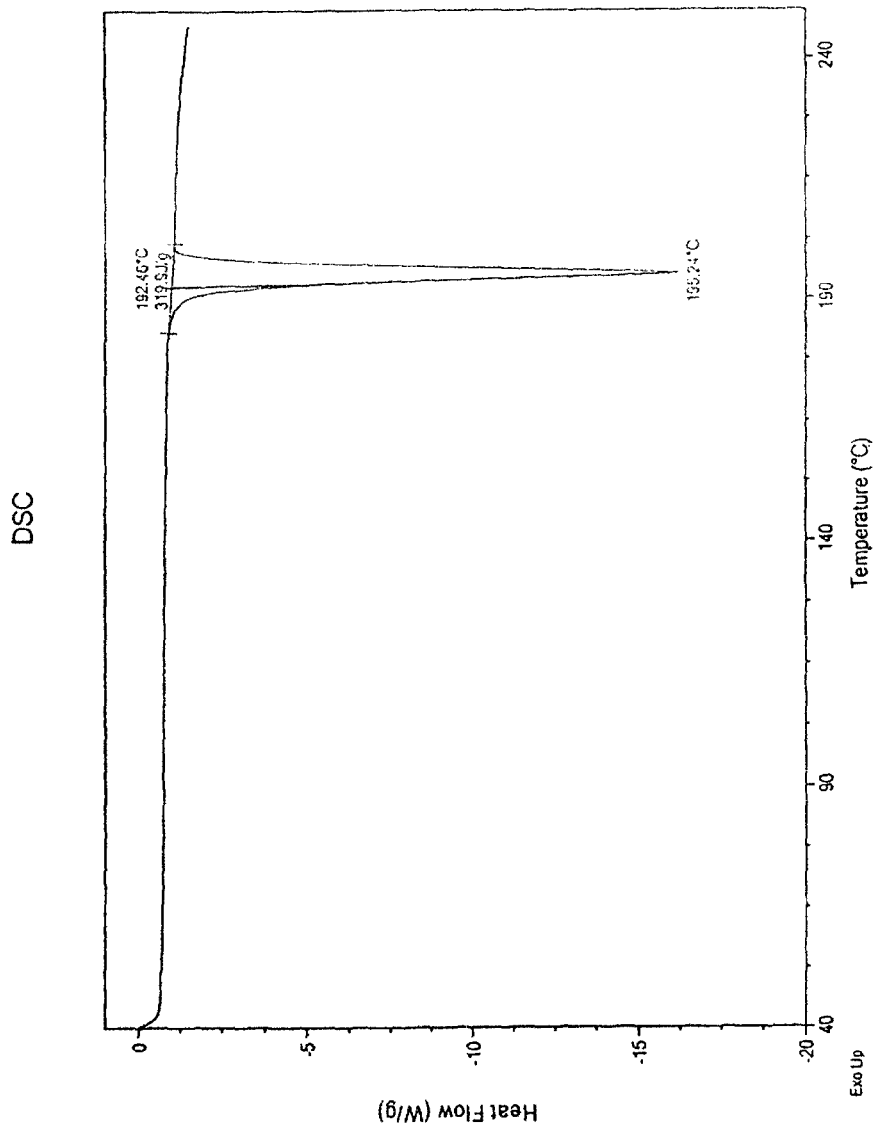

FIG. 3: Illustrates the DSC thermogram of crystalline form-M of ethyl 3-(2-((4-cyanophenylamino)methyl)-1-methyl-N-(pyridin-2-yl)-1H-benzo[d]imidazole-5-carboxamido) propanoate mesylate compound of formula-10.

Figure 4:
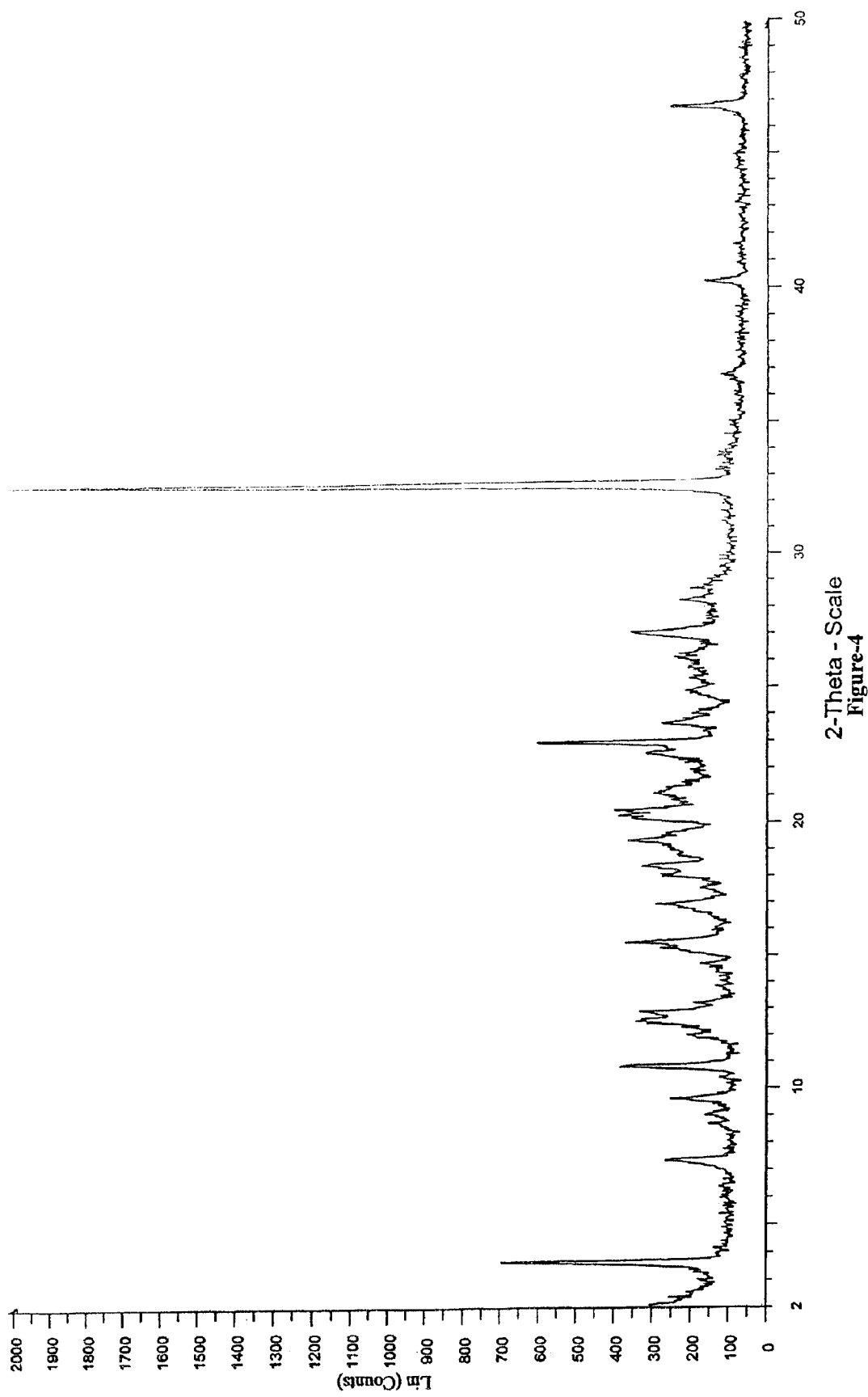

FIG. 4: Illustrates the PXRD pattern of crystalline form-N of ethyl 3-(2-((4-carbamimidoylphenylamino)methyl)-1-methyl-N-(pyridin-2-yl)-1H-benzo[d]imidazole-5-carboxamido)propanoate mesylate compound of formula-11.

Figure 5:
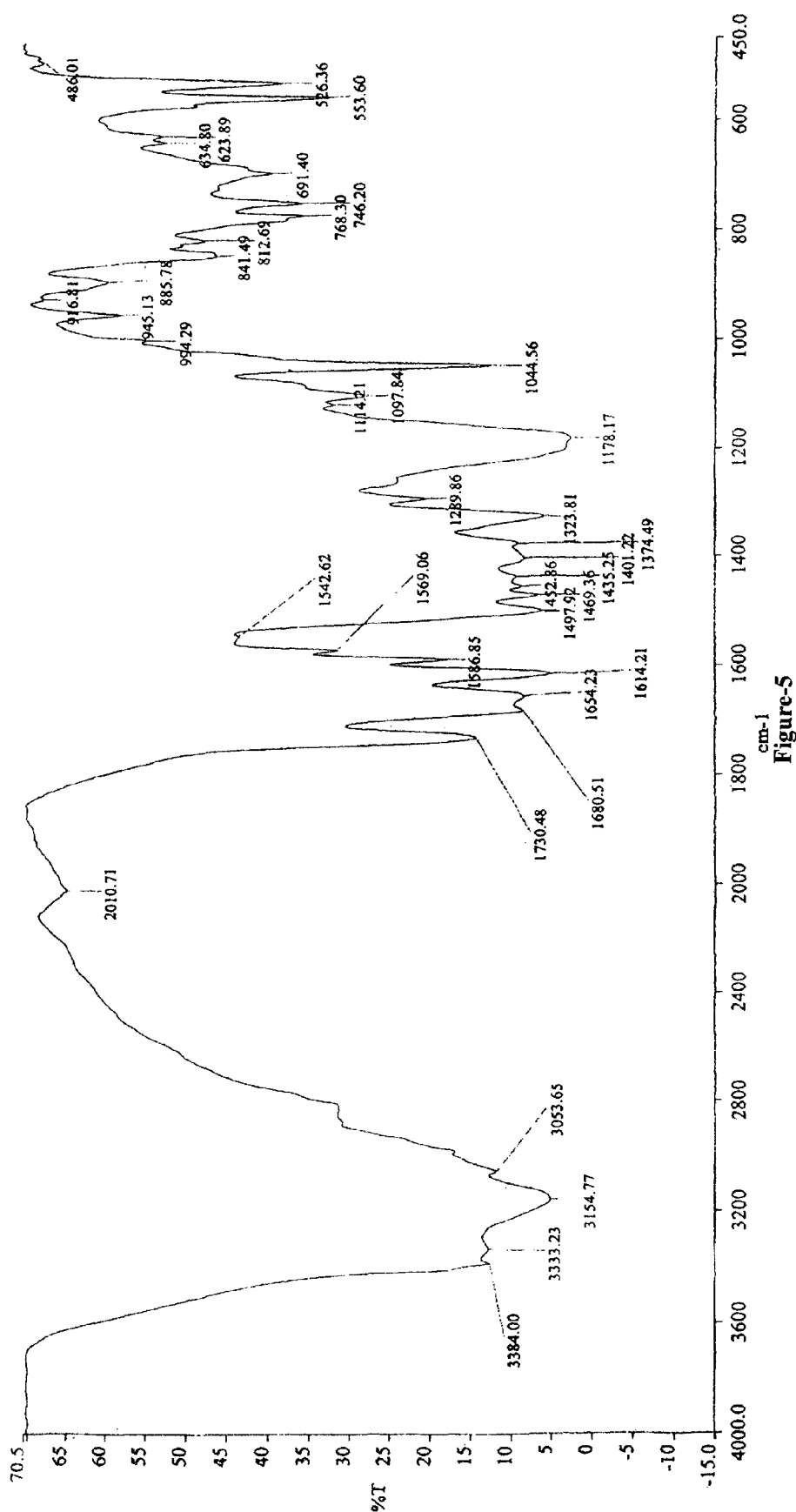

FIG. 5: Illustrates the IR spectrum of crystalline form-N of ethyl 3-(2-((4-carbamimidoylphenylamino)methyl)-1-methyl-N-(pyridin-2-yl)-1H-benzo[d]imidazole-5-carboxamido) propanoate mesylate compound of formula-11.

Figure 6:
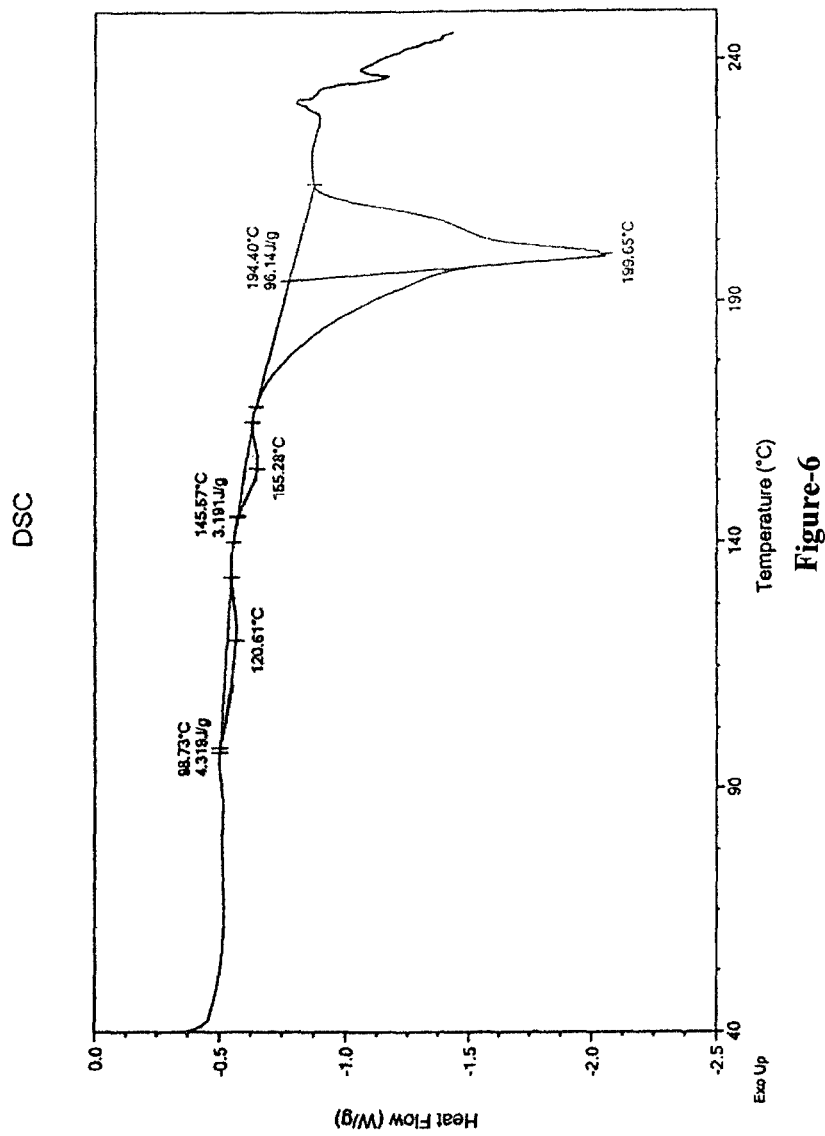

FIG. 6: Illustrates the DSC thermogram of crystalline form-N of ethyl 3-(2-((4-carbamimidoylphenylamino)methyl)-1-methyl-N-(pyridin-2-yl)-1H-benzo[d]imidazole-5-carboxamido) propanoate mesylate compound of formula-11.

Figure 7:
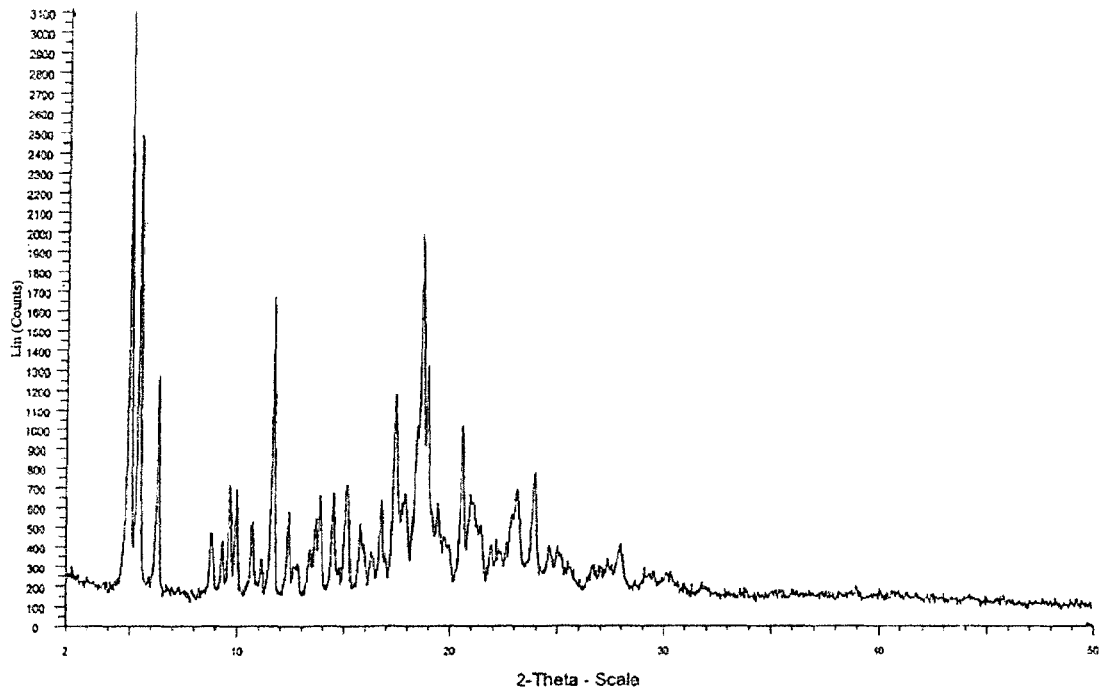

FIG. 7: Illustrates the PXRD pattern of crystalline form-M of Dabigatran etexilate (–)-camphor sulfonate.

Figure 8:
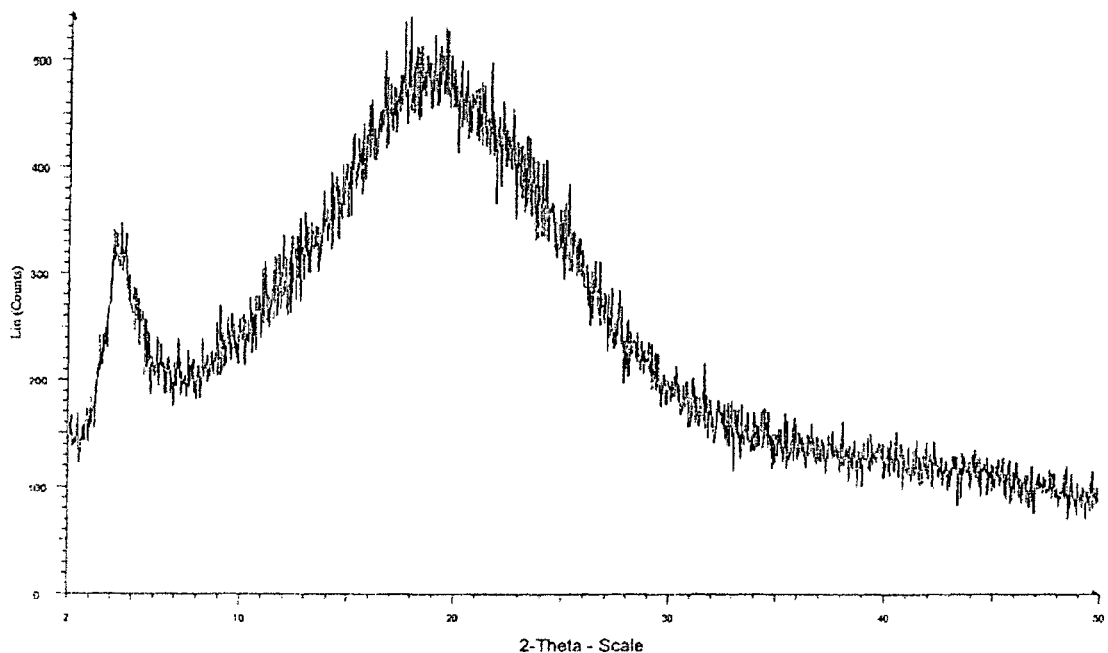

FIG. 8: Illustrates the PXRD pattern of amorphous Dabigatran etexilate (–)-camphor sulfonate.

Figure 9:
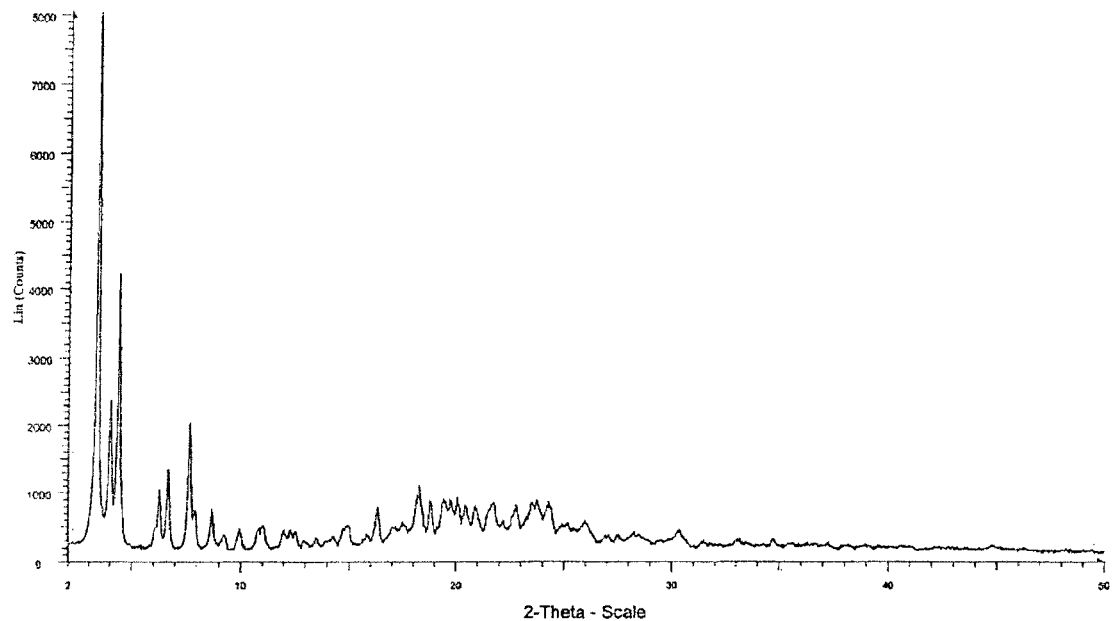

FIG. 9: Illustrates the PXRD pattern of crystalline form-S of Dabigatran etexilate oxalate.

Figure 10:
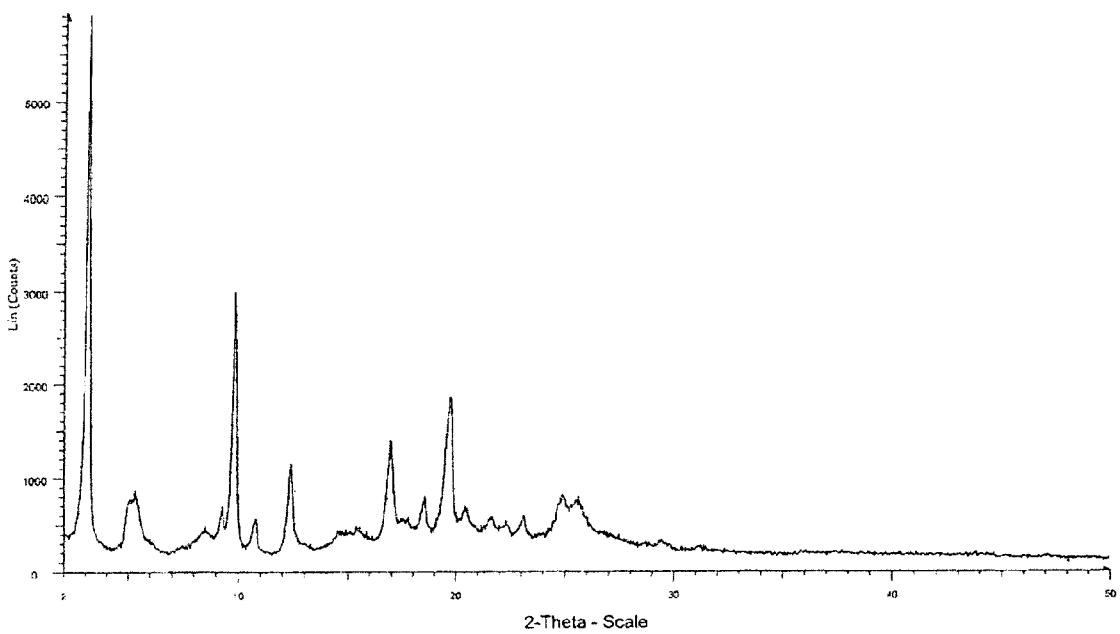

FIG. 10: Illustrates the PXRD pattern of crystalline form-N of Dabigatran etexilate fumarate.

FIG. 11: Illustrates the microscopic photographs of Dabigatran etexilate mesylate compound of formula-1a.

DETAILED DESCRIPTION OF THE INVENTION

The term "suitable solvent" used herein the present invention refers, but not limited to "hydrocarbon solvents" such as n-hexane, n-heptane, cyclohexane, pet.ether, benzene, toluene, xylene, perfluorobenzene and the like; "chloro solvents" such as dichloromethane, dichloroethane, carbon tetrachloride, chloroform and the like; "ester solvents" such as ethyl acetate, methyl acetate, propyl acetate, isopropyl acetate and the like; "polar aprotic solvents" such as dimethyl acetamide, dimethyl formamide, dimethyl sulfoxide and the like; "ether solvents" such as dimethyl ether, diethyl ether, diisopropyl ether, methyl tert-butyl ether, tetrahydrofuran, 1,4-dioxane, 1,2-dimethoxy ethane and the like; "alcoholic solvents" such as methanol, ethanol, propanol, isopropanol, n-butanol, isobutanol, tert-butanol and the like; "ketone solvents" such as acetone, propanone, methylethyl ketone, methylisobutyl ketone, methylisopropyl ketone, 4-hydroxy-4-methyl pentanone and the like; "nitrile solvents" like acetonitrile, propionitrile and the like; "nitro solvents" like nitro methane, nitro ethane and the like and "polar solvents" such as water; and/or their mixtures.

The term "suitable base" used herein the present invention refers, but not limited to "inorganic bases" selected from alkali and alkaline earth metal hydroxides, alkoxides, carbonates, bicarbonates and hydrides such as sodium hydroxide, potassium hydroxide, lithium hydroxide, sodium methoxide, potassium methoxide, sodium ethoxide, potassium tert-butoxide, sodium tert-butoxide, sodium carbonate, potassium carbonate, sodium bicarbonate, potassium bicarbonate, sodium hydride, potassium hydride and the like; and "organic bases" like diisopropyl amine, diisopropyl ethyl amine, diisobutyl amine, isopropyl ethylamine, triethyl amine, pyridine, 4-dimethylamino pyridine, N-methyl morpholine, piperidine and/or mixtures thereof.

The conversion of acid to acid chloride wherever necessary in the present invention is carried out by using thionyl chloride, oxalyl chloride, phosphorous trichloride, phosphorous pentachloride and the like.

The main object of the present invention is to provide novel salts of benzimidazole derivatives, such as mesylate salt of ethyl 3-(2-((4-cyanophenylamino)methyl)-1-methyl-N-(pyridin-2-yl)-1H-benzo[d]imidazole-5-carboxamido)propanoate compound of formula-10, mesylate salt of ethyl 3-(2-((4-carbamimidoylphenylamino)methyl)-1-methyl-N-(pyridin-2-yl)-1H-benzo[d]imidazole-5-carboxamido) propanoate compound of formula-11 and camphor sulfonate salt of Dabigatran etexilate. The present invention also provides polymorphs for these novel salts.

Further, the present invention provides novel polymorphic forms of Dabigatran etexilate salts, such as oxalate and fumarate salts.

Further, the object of the present invention is to provide an improved process for the preparation of diamine compound of formula-7, which is a key intermediate in the synthesis of Dabigatran etexilate compound of formula-1 and its salts.

The first aspect of the present invention provides a process for the preparation of ethyl 3-(3-amino-4-(methylamino)-N-(pyridin-2-yl)benzamido)propanoate compound of formula-7,

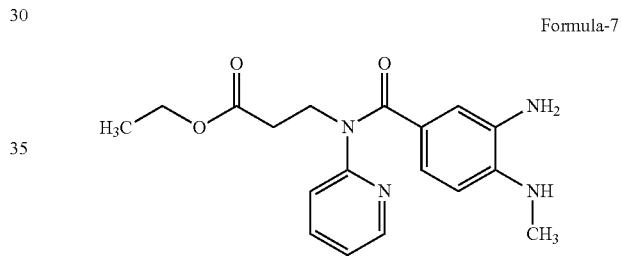

Formula-7 comprising of reducing ethyl 3-(4-(methylamino)-3-nitro-N-(pyridin-2-yl)benzamido) propanoate compound of formula-6

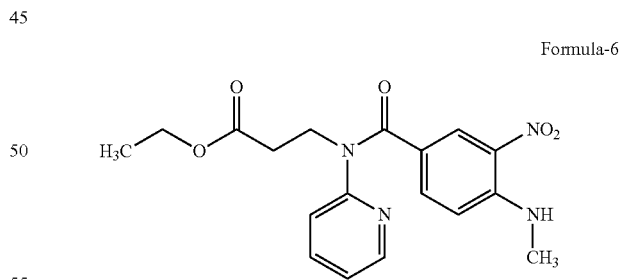

Formula-6 with Fe-acetic acid (or) Fe-hydrochloric acid in a suitable solvent.

Wherein, the suitable solvent is selected from ether solvents, hydrocarbon solvents, chloro solvents, ester solvents, alcoholic solvents, polar solvents, polar aprotic solvents and/or mixtures thereof.

The amount of Fe used in the present invention for the reduction of 1 mole of compound of formula-6 is in the range of 2-8 molar equivalents, preferably 3-7 molar equivalents.

The amount of acetic acid (or) hydrochloric acid used in the present invention for reduction of 1 mole of compound of formula-6 is in the range of 1-7 molar equivalents, preferably 2-6 molar equivalents and more preferably 3-5 molar equivalents.

The reduction was carried out at a temperature ranging from 10° C. to 120° C., preferably at 40° C. to 75° C.

A preferred embodiment of the present invention provides a process for the preparation of diamine compound of formula-7, comprising of reducing the nitro compound of formula-6 with Fe-acetic acid in aqueous tetrahydrofuran at a reflux temperature.

Another preferred embodiment of the present invention provides a process for the preparation of diamine compound of formula-7, comprising of reducing the nitro compound of formula-6 with Fe-hydrochloric acid in aqueous tetrahydrofuran at a reflux temperature.

In the above reduction step, Fe in combination with ammonium chloride can also be used as a reducing agent.

Further, the ethyl 3-(3-amino-4-(methylamino)-N-(pyridin-2-yl)benzamido)propanoate compound of formula-7 obtained by the present invention can be utilized in the synthesis of Dabigatran etexilate compound of formula-1, which in-turn useful in the synthesis of its salts such as mesylate, (−)-camphor sulfonate, (+)-camphor sulfonate, oxalate and fumarate.

The second aspect of the present invention provides ethyl 3-(2-((4-cyano phenylamino)methyl)-1-methyl-N-(pyridin-2-yl)-1H-benzo[d]imidazole-5-carboxamido)propanoate mesylate compound of formula-10.

Formula-10

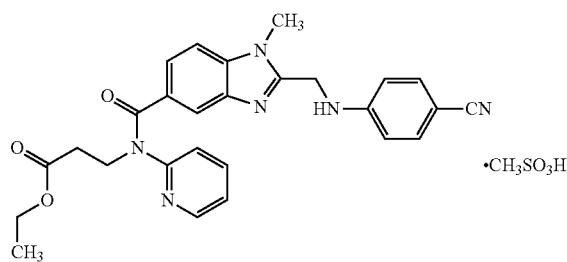

Figure 1:
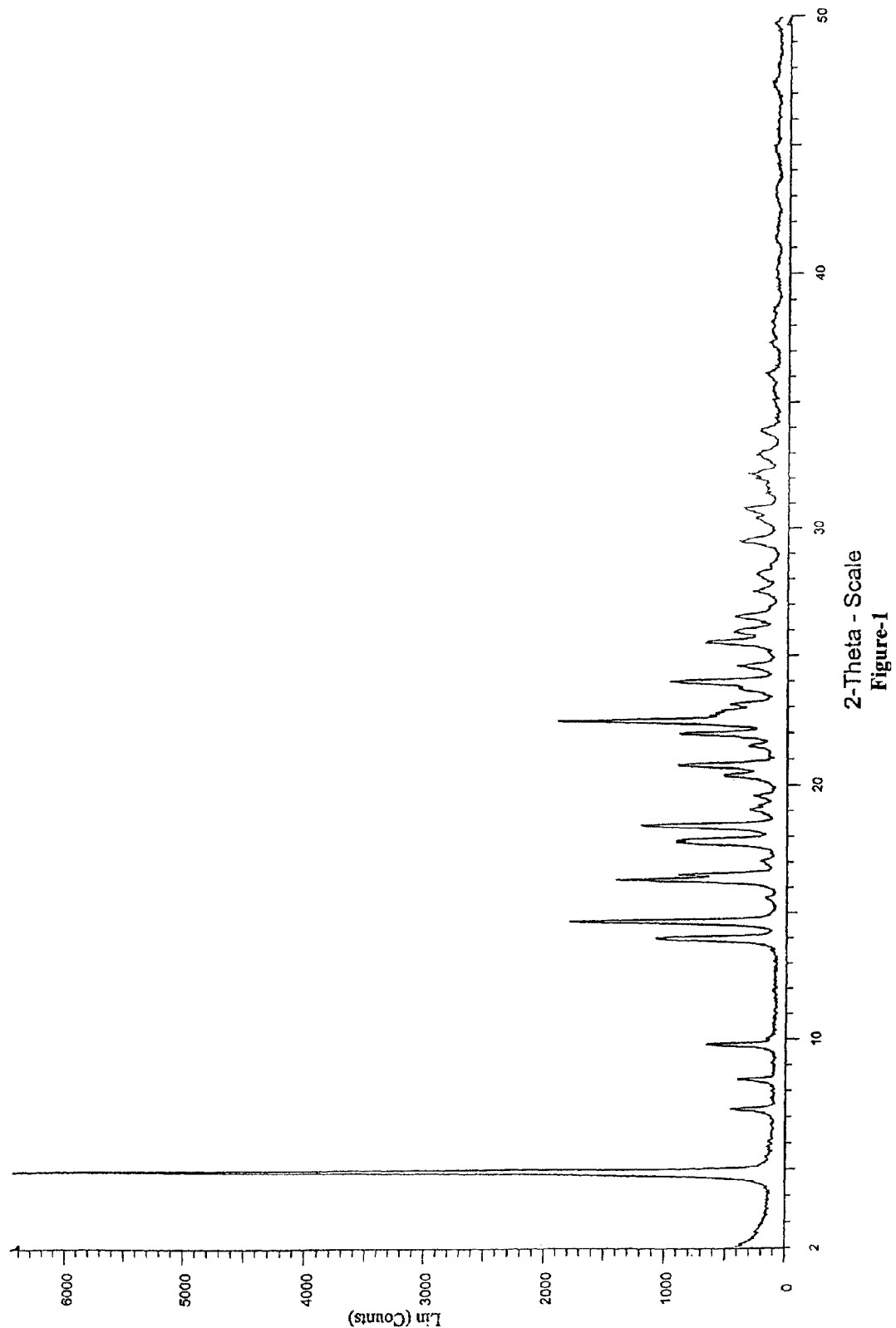
FIG. 1: Illustrates the PXRD pattern of crystalline form-M of ethyl 3-(2-((4-cyano phenylamino)methyl)-1-methyl-N-

Further, the present invention also provides crystalline form of ethyl 3-(2-((4-cyanophenylamino)methyl)-1-methyl-N-(pyridin-2-yl)-1H-benzo[d]imidazole-5-carboxamido) propanoate mesylate compound of formula-10 (herein designated as crystalline form-M). The crystalline form-M of compound of formula-10 characterized by:
  a) its powder XRD having peaks at 4.9, 14.0, 14.6, 16.3, 18.4 and 22.4±0.2 degrees of 2θ, and is further characterized by peaks at 16.5, 17.8, 20.8 and 24.0±0.2 degrees of 2θ and substantially as shown in figure-1;
  b) IR spectrum showing absorption peaks at 2216, 3345, 1032 and 1174 cm$^{-1}$ and substantially as shown in figure-2; and
  c) its DSC thermogram showing endotherm at 195.24° C. as shown in figure-3.

The usage of the above crystalline form of formula-10 will enhances the purity and yield of final compound i.e. Dabigatran etexilate and as well as its salts like mesylate, oxalate, fumarate and camphor sulfonate salts.

Further, the second aspect of the present invention also provides a process for the preparation of ethyl 3-(2-(4-cyanophenylamino)methyl)-1-methyl-N-(pyridin-2-yl)-1H-benzo[d]imidazole-5-carboxamido) propanoate mesylate compound of formula-10, comprising of reacting ethyl 3-(3-amino-4-(methylamino)-N-(pyridin-2-yl)benzamido) propanoate compound of formula-7 with 2-(4-cyanophenyl amino)acetic acid compound of formula-9

Formula-9

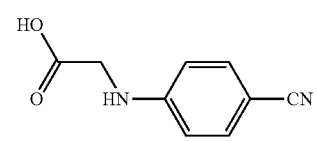

in presence of a suitable condensing agent in a suitable solvent, and the obtained compound in-situ converted into its mesylate salt compound of formula-10 by reacting with methane sulfonic acid in a suitable solvent.

Wherein, the "suitable solvent" used for the reaction of compound of formula-7 and compound of formula-9 is selected from ether solvents, hydrocarbon solvents, chloro solvents, ester solvents, ketone solvents and polar aprotic solvent and/or mixtures thereof; the "suitable solvent" used for mesylate formation is selected from ester solvents, alcoholic solvents, ether solvents, chloro solvents and ketone solvents; and The "suitable condensing agent" is selected from pivaloyl chloride, polyphosphoric acid, carbodiimides such as N,N$^1$-diisopropylcarbodiimide (DIC), 1-ethyl-3-(3-dimethylaminopropyl) carbodiimide (EDC), N,N$^1$-dicyclohexyl carbodiimide (DCC); alkyl or aryl chloroformates such as ethyl chloroformates, benzyl chloroformates, para-nitrophenyl chloroformates; 3-hydroxy-3,4-dihydro-1,2,3-benzotriazin-4-one, diethylphosphorarocyanidate (DEPC), diphenylphosphoroazidate (DPPA), P$_2$O$_5$, 3-(diethoxyphosphoryloxy)-1,2,3-benzotriazine-4(3H)-one (DEPBT), N,N'-carbonyl diimidazole. The carbodiimides can be used optionally in combination with 1-hydroxybenzotriazole (HOBt), 1-hydroxy-7-azatriazole (HOAt), 1-hydroxy-1H-1,2,3-triazole-4-carboxylate (HOCt), N-hydroxy succinamide (HOSu), (2-(1H-benzotriazol-1-yl)-1,1,3,3-tetramethyluronium tetrafluoro borate (TBTU), dimethylamino pyridine (DMAP). The alkyl (or) aryl chloroformates can be used optionally in combination with a base.

A preferred embodiment of the present invention provides a process for the preparation of ethyl 3-(2-((4-cyanophenylamino)methyl)-1-methyl-N-(pyridin-2-yl)-1H-benzo[d]imidazole-5-carboxamido) propanoate mesylate compound of formula-10, comprising of reacting ethyl 3-(3-amino-4-(methyl amino)-N-(pyridin-2-yl)benzamido) propanoate compound of formula-7 with 2-(4-cyano phenyl amino) acetic acid compound of formula-9 in presence of N,N-carbonyldiimidazole in tetrahydrofuran, and the obtained compound in-situ converted into its mesylate compound of formula-10 by reacting with methane sulfonic acid in acetone.

The third aspect of the present invention relates to ethyl 3-(2-((4-carbamimidoylphenyl amino)methyl)-1-methyl-N-(pyridin-2-yl)-1H-benzo[d]imidazole-5-carboxamido)propanoate mesylate compound of formula-11.

Formula-11

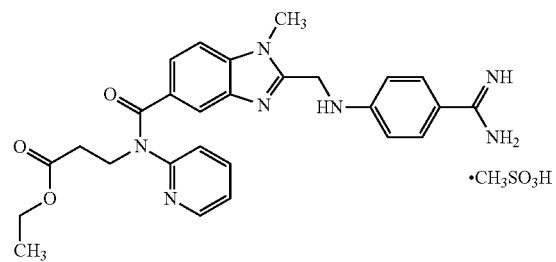

Further, the present invention also provides the crystalline form of ethyl 3-(2-((4-carbamimidoylphenylamino)methyl)-1-methyl-N-(pyridin-2-yl)-1H-benzo[d]imidazole-5-carboxamido)propanoate mesylate compound of formula-11 (herein designated as crystalline form-N). The crystalline form-N of compound of formula-11 characterized by:
 a) its powder XRD having peaks at 3.6, 10.8, 22.9 and 32.6±0.2 degrees of 2θ, and is further characterized by peaks at 12.8, 15.4, 20.2, 27.0 and 46.8±0.2 degrees of 2θ and substantially as shown in figure-4;
 b) its IR spectrum showing absorption peaks at 1044, 1179 and 3155 cm-1 and substantially as shown in figure-5; and
 c) its DSC thermogram showing endotherm at 199.65° C. as shown in figure-6.

The usage of crystalline solid of compound of formula-11 will enhances the purity and yield of final compound i.e. Dabigatran etexilate and its salts like mesylate, oxalate, fumarate and camphor sulfonate salts.

Further, the third aspect of the present invention also provides a process for the preparation of ethyl 3-(2-((4-carbamimidoylphenylamino)methyl)-1-methyl-N-(pyridin-2-yl)-1H-benzo[d]imidazole-5-carboxamido) propanoate mesylate compound' of formula-11, comprising of treating ethyl 3-(2-((4-cyano phenyl amino)methyl)-1-methyl-N-(pyridin-2-yl)-1H-benzo[d]imidazole-5-carboxamido) propanoate mesylate compound of formula-10 with a suitable ammonia source and/or ammonia gas in presence of hydrogen chloride gas and Lewis acid in a suitable solvent to provide compound of formula-11.
 Wherein, the "suitable solvent" is selected from alcoholic solvents, chloro solvents, ether solvents, ketone solvents and/ or mixtures thereof;
 The "Lewis acid" used is selected from aluminium chloride ($AlCl_3$), aluminium bromide ($AlBr_3$), boron trifluoride ($BF_3$), boron trichloride ($BCl_3$), ferric chloride ($FeCl_3$), tin(IV) chloride ($SnCl_4$), calcium chloride ($CaCl_2$) and calcium chloride dihydrate ($CaCl_2.2H_2O$), preferably calcium chloride and calcium chloride dihydrate and/or mixture thereof;
 The "suitable ammonia source" is selected from ammonium carbonate, ammonium formate, formamide, ammonia gas, ammonium carbamate, ammonium formate, ammonium phosphate, ammonium acetate, ammonium fluoride, ammonium bromide, ammonium chloride, ammonium iodide, ammonium iodate, ammonium citrate, ammonium chromate, ammonium dichromate, ammonium hydroxide, ammonium lactate, ammonium molybdate, ammonium nitrate, ammonium oxalate, ammonium sulfate, ammonium sulfide, ammonium tartrate, ammonium triflate, ammonium thiocyanate, ammonium dihydrogen phosphate, urea, methyl carbamate, ethyl carbamate, propyl carbamate and t-butyl carbamate.

A preferred embodiment of the present invention provides a process for the preparation of ethyl 3-(2-((4-carbamimidoylphenylamino)methyl)-1-methyl-N-(pyridin-2-yl)-1H-benzo[d]imidazole-5-carboxamido)propanoate mesylate compound of formula-11, comprising of treating ethyl 3-(2-((4-cyanophenylamino)methyl)-1-methyl-N-(pyridin-2-yl)-1H-benzo[d]imidazole-5-carboxamido)propanoate mesylate compound of formula-10 with ammonium carbonate in presence of ammonia gas, hydrogen chloride gas and calcium chloride in ethanol to provide compound of formula-11.

The fourth aspect of the present invention provides a process for the purification of ethyl 3-(2-((4-carbamimidoylphenylamino)methyl)-1-methyl-N-(pyridin-2-yl)-1H-benzo[d]imidazole-5-carboxamido)propanoate mesylate compound of formula-11, comprising of:
 a) Dissolving the ethyl 3-(2-((4-carbamimidoylphenylamino)methyl)-1-methyl-N-(pyridin-2-yl)-1H-benzo[d]imidazole-5-carboxamido)propanoate mesylate salt compound of formula-11 in an alcoholic solvent,
 b) adding a suitable non-polar solvent to the above obtained solution,
 c) stirring the solution,
 d) filtering the obtained solid and drying to get the pure compound of formula-11.
 Wherein, the "suitable non-polar solvent" is selected from ether solvents, ester solvents, ketone solvents, nitrile solvents, hydrocarbon solvents, chloro solvents etc.

A preferred embodiment of the present invention provides a process for the purification of ethyl 3-(2-((4-carbamimidoylphenylamino)methyl)-1-methyl-N-(pyridin-2-yl)-1H-benzo[d]imidazole-5-carboxamido)propanoate mesylate compound of formula-11, comprising of:
 a) Dissolving the ethyl 3-(2-((4-carbamimidoylphenylamino)methyl)-1-methyl-N-(pyridin-2-yl)-1H-benzo[d]imidazole-5-carboxamido)propanoate mesylate salt compound of formula-11 in ethanol,
 b) adding ethyl acetate to the above obtained solution,
 c) stirring the solution,
 d) filtering the obtained solid and drying to get the pure compound of formula-11.

The crude ethyl 3-(2-((4-carbamimidoylphenylamino)methyl)-1-methyl-N-(pyridin-2-yl)-1H-benzo[d]imidazole-5-carboxamido)propanoate mesylate compound of formula-11 is having the purity of 70-80% by HPLC which inturns reduces the purity of the subsequent intermediates as well as the final compound, if utilized the crude compound. The present inventors has purified the above compound of formula-11 by the above purification method which enhances the purity by 95.60% HPLC which also enhances the purity of the final compound i.e., Dabigatran etexilate and its salts.

The fifth aspect of the present invention provides a process for the preparation of 1-methyl-2-[N-[4-(N-n-hexyloxycarbonylamidino)phenyl]aminomethyl]benzimidazol-5-yl-carboxylic acid-N-(2-pyridyl)-N-(2-ethoxycarbonylethyl) amide compound of formula-1, comprising of:
 a) Reacting n-hexanol and N,N-carbonyldiimidazole in a suitable solvent to provide an amide compound,
 b) reacting the amide compound of step-(a) in-situ with ethyl 3-(2-((4-carbamimidoyl phenylamino)methyl)-1-methyl-N-(pyridin-2-yl)-1H-benzo[d]imidazole-5-carboxamido) propanoate mesylate compound of formula-11 in presence of a suitable base in a suitable solvent provides the compound of formula-1.
 Wherein,
  In step-a) the "suitable solvent" is selected form chloro solvents, ester solvent, ether solvents, ketone solvents, polar aprotic solvents and nitrile solvents; and
  In step-b) the "suitable solvent" is organic solvent selected from polar aprotic solvent, ether solvents, ester solvents, nitrile solvents and ketone solvent, or mixture of water and organic solvent; the "suitable base" is selected from alkali metal carbonates such as sodium carbonate, potassium carbonate; alkali metal bicarbonates like sodium bicarbonate and potassium bicarbonate and the like; and the reaction was carried out at a temperature ranging from 10-50° C., preferably 25-35° C.

A preferred embodiment of the present invention provides a process for the preparation of 1-methyl-2-[N-[4-(N-n-hexyloxycarbonylamidino)phenyl]aminomethyl]benzimidazol-5-yl-carboxylic acid-N-(2-pyridyl)-N-(2-ethoxycarbonylethyl)amide compound of formula-1, comprising of:

a) Reacting n-hexanol and N, N-carbonyldiimidazole in dichloromethane to provide an amide compound, b) reacting the amide compound of step-a) in-situ with ethyl 3-(2-((4-carbamimidoyl phenylamino)methyl)-1-methyl-N-(pyridin-2-yl)-1H-benzo[d]imidazole-5-carboxamido) propanoate mesylate compound of formula-11 in presence of potassium carbonate in aqueous acetonitrile provides the compound of formula-1

The usage of purified mesylate salt of ethyl 3-(2-((4-carbamimidoylphenylamino)methyl)-1-methyl-N-(pyridin-2-yl)-1H-benzo[d]imidazole-5-carboxamido)propanoate compound of formula-11 will result in the formation of Dabigatran etexilate with purity 99.6% by HPLC, which in-turn enhances the purity of final compound i.e. Dabigatran etexilate mesylate.

Alternatively, 1-methyl-2-[N-[4-(N-n-hexyloxycarbonylamidino)phenyl]amino methyl]benzimidazol-5-yl-carboxylicacid-N-(2-pyridyl)-N-(2-ethoxycarbonylethyl) amide compound of formula-1 can be prepared from ethyl 3-(2-((4-carbamimidoylphenyl amino)methyl)-1-methyl-N-(pyridin-2-yl)-1H-benzo[d]imidazole-5-carboxamido)propanoate mesylate compound of formula-11 and n-hexylchloroformate in presence of a suitable base in a suitable solvent.

Wherein, the "suitable base" is selected from alkali metal carbonate such as sodium carbonate, potassium carbonate; and alkali metal bicarbonates such as sodium bicarbonate and potassium bicarbonate; organic bases selected from triethylamine, isopropyl ethylamine, diisopropyl amine, diisopropyl ethylamine, N-methyl morpholine, piperidine, pyridine and mixtures thereof.

Alternatively, 1-methyl-2-[N-[4-(N-n-hexyloxycarbonylamidino)phenyl]amino methyl]benzimidazol-5-yl-carboxylicacid-N-(2-pyridyl)-N-(2-ethoxycarbonylethyl)amide compound of formula-1 can be prepared from ethyl 3-(2-((4-carbamimidoylphenylamino)methyl)-1-methyl-N-(pyridin-2-yl)-1H-benzo[d]imidazole-5-carboxamido)propanoate mesylate compound of formula-11 and n-hexanol in presence of a suitable condensing agent and a suitable base in a suitable solvent.

Wherein, the suitable condensing agent is same as defined above.

The sixth aspect of the present invention provides a process for the preparation of 1-methyl-2-[N-[4-(N-n-hexyloxycarbonylamidino)phenyl]aminomethyl]benzimidazol-5-yl-carboxylicacid-N-(2-pyridyl)-N-(2-ethoxycarbonylethyl)amide compound of formula-1, comprising of:

a) Reacting 2-aminopyridine compound of formula-2 with ethyl acrylate compound of formula-3 at a temperature of 95-100° C. provides ethyl 3-(pyridin-2-ylamino)propanoate compound of formula-4,

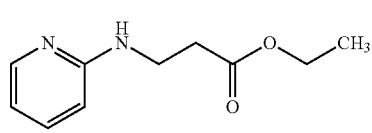

Formula-4 b) reacting 4-chloro-3-nitrobenzoic acid compound of formula-8

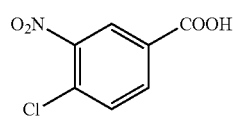

Formula-8 with methyl amine to provide 4-(methylamino)-3-nitrobenzoic acid compound of formula-5,

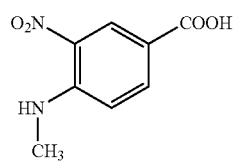

Formula-5 c) condensing the compound of formula-5 obtained in step-(b) with ethyl 3-(pyridin-2-ylamino) propanoate compound of formula-4 obtained in step-(a) in a suitable solvent to provide nitro compound of formula-6, d) reducing the nitro compound of formula-6 in-situ with Fe-acetic acid (or) Fe-hydrochloric acid in a suitable solvent to provide its corresponding diamine compound of formula-7, e) reacting the compound of formula-7 with 2-(4-cyanophenyl amino)acetic acid compound of formula-9 in presence of a suitable condensing agent in a suitable solvent, and the obtained compound in-situ converted into its mesylate salt compound of formula-10 by reacting with methane sulfonic acid in a suitable solvent, f) treating the compound of formula-10 with a suitable ammonia source and/or ammonia gas in presence of hydrogen chloride gas and Lewis acid in a suitable solvent to provide compound of formula-11, g) reacting n-hexanol and N,N-carbonyldiimidazole in a suitable solvent to provide an amide compound, h) reacting the amide compound of step-(g) in-situ with the compound of formula-11 in presence of a suitable base in a suitable solvent provides 1-methyl-2-[N-[4-(N-n-hexyloxycarbonylamidino)phenyl]aminomethyl]benzimidazol-5-yl-carboxylicacid-N-(2-pyridyl)-N-(2-ethoxy carbonylethyl)amide compound of formula-1.

Wherein,

In step-c) the "suitable solvent" is selected from hydrocarbon solvents, ester solvents, ether solvents, polar aprotic solvents and/or mixtures thereof;

In step-d) the "suitable solvent" is selected from ether solvents, hydrocarbon solvents, chloro solvents, ester solvents, alcoholic solvents, polar solvents, polar aprotic solvents and/or mixtures thereof.

In step-e) the "suitable condensing agent" and "suitable solvents" are same as defined in second aspect of the present invention;

In step-f) the "suitable ammonia source", "Lewis acid" and "suitable solvent" are same as defined in third aspect of the present invention;

In step-g) the "suitable solvent" is same as defined in step-(a) of fifth aspect of the present invention;

In step-h) the suitable base and suitable solvent are same as defined in step-(b) of fifth aspect of the present invention.

The condensation of compound of formula-4 with compound of formula-5 in the step-(c) of above aspect is carried out by using a suitable condensing agent (or) by converting the acid compound of formula-5 into its corresponding acid chloride (or) its derivatives by the known methods in the art and then condensed with compound of formula-4 in the presence or absence of a suitable base selected from alkali and alkaline earth metal hydroxides, alkoxides, carbonates, bicarbonates, hydrides and organic bases to provide nitro compound of formula-6.

The nitro compound of formula-6 in the above aspect can be isolated from a suitable solvent and then reduced with Fe-acetic acid (or) Fe-hydrochloric acid in a suitable solvent selected from ether solvents, hydrocarbon solvents, chloro solvents, ester solvents, alcoholic solvents, polar solvents, polar aprotic solvents and/or mixtures thereof to provide its corresponding diamine compound of formula-7.

A preferred embodiment of the present invention provides a process for the preparation of 1-methyl-2-[N-[4-(N-n-hexyloxycarbonylamidino)phenyl]aminomethyl]benzimidazol-5-yl-carboxylicacid-N-(2-pyridyl)-N-(2-ethoxycarbonyl-ethyl)amide compound of formula-1, comprising of:
 a) Reacting 2-aminopyridine compound of formula-2 with ethyl acrylate compound of formula-3 at a temperature of 95-100° C. provides ethyl 3-(pyridin-2-ylamino)propanoate compound of formula-4,
 b) reacting 4-chloro-3-nitrobenzoic acid compound of formula-8 with methyl amine to provide 4-(methylamino)-3-nitrobenzoic acid compound of formula-5,
 c) reacting the compound of formula-5 obtained in step-(b) with thionyl chloride in a mixture of toluene and dimethylformamide to provide its corresponding acid chloride,
 d) condensing the acid chloride compound obtained in step-(c) in-situ with ethyl 3-(pyridin-2-ylamino) propanoate compound of formula-4 obtained in step-(a) in presence of triethylamine in toluene to provide nitro compound of formula-6,
 e) reducing the nitro compound of formula-6 in-situ with Fe-acetic acid in aqueous tetrahydrofuran in a suitable solvent to provide its corresponding diamine compound of formula-7,
 f) reacting the compound of formula-7 with 2-(4-cyanophenylamino)acetic acid compound of formula-9 in presence of N,N-carbonyldiimidazole in tetrahydrofuran, and the obtained compound is in-situ converted into its mesylate compound of formula-10 by reacting with methane sulfonic acid in acetone,
 g) treating the compound of formula-10 with ammonium carbonate in presence of ammonia gas, hydrogen chloride gas and calcium chloride in ethanol provides compound of formula-11,
 h) reacting n-hexanol and N,N-carbonyldiimidazole in dichloromethane to provide an amide compound,
 i) reacting the amide compound of step-(h) in-situ with the compound of formula-11 in presence of potassium carbonate in aqueous acetonitrile provides the compound of formula-1.

The 2-amino pyridine compound of formula-2, ethyl acrylate compound of formula-3 and 4-chloro-3-nitrobenzoic acid compound of formula-8 are commercially available.

The seventh aspect of the present invention provides (−)-camphor sulfonate salt of Dabigatran etexilate.

Further, the seventh aspect of the present invention also provides a process for the preparation of Dabigatran etexilate (−)-camphor sulfonate comprising of reacting Dabigatran etexilate with (−)-camphor sulfonic acid in a suitable solvent to provide (−)-camphor sulfonate salt of Dabigatran etexilate.

Wherein, the suitable solvent is selected from ketone solvents, ether solvents, alcoholic solvents, ester solvents, polar aprotic solvents, polar solvents and/or mixtures thereof.

The eighth aspect of the present invention relates to novel polymorph of Dabigatran etexilate (−)-camphor sulfonate (herein designated as crystalline form-M). The crystalline form-M of Dabigatran etexilate (−)-camphor sulfonate is characterized by its powder X-ray diffraction pattern having peaks at 4.9, 5.3 and 18.6±0.2 degrees of 2θ values.

The crystalline form-M of Dabigatran etexilate (−)-camphor sulfonate is further characterized by additional peaks at 6.2, 11.6, 17.3, 18.8 and 20.5±0.2 degrees of 2θ values as illustrated in figure-7.

Further, the eighth aspect of the present invention also provides a process for the preparation of crystalline form-M of Dabigatran etexilate (−)-camphor sulfonate, comprising of:
 a) Reacting Dabigatran etexilate with (−)-camphor sulfonic acid in a suitable solvent selected from ketone solvents, ether solvents, alcoholic solvents, ester solvents, polar aprotic solvents, polar solvents and/or mixtures thereof,
 b) distilling off the solvent completely from the reaction mixture,
 c) adding alcoholic solvent to the reaction mixture,
 d) adding an ether solvent to the reaction mixture,
 e) stirring the reaction mixture,
 f) filtering the precipitated solid and then dried to get crystalline form-M of Dabigatran etexilate (−)-camphor sulfonate.

A preferred embodiment of the present invention provides a process for the preparation of crystalline form-M of Dabigatran etexilate (−)-camphor sulfonate, comprising of:
 a) Reacting Dabigatran etexilate with (−)-camphor sulfonic acid in acetone,
 b) distilling off acetone completely from the reaction mixture,
 c) adding ethanol to the reaction mixture,
 d) adding methyl tertiary butyl ether to the reaction mixture,
 e) stirring the reaction mixture,
 f) filtering the precipitated solid and then dried to get crystalline form-M of Dabigatran etexilate (−)-camphor sulfonate.

The ninth aspect of the present invention relates to amorphous form of Dabigatran etexilate (−)-camphor sulfonate characterized by its powder X-ray diffraction pattern as illustrated in figure-8.

Further, the ninth aspect of the present invention also provides a process for the preparation of an amorphous Dabigatran etexilate (−)-camphor sulfonate, comprising of:
 a) Reacting Dabigatran etexilate with (−)-camphor sulfonic acid in a suitable solvent selected from ketone solvents, ether solvents, alcoholic solvents, ester solvents, polar aprotic solvents, polar solvents and/or mixtures thereof,
 b) concentrating the reaction mixture,
 c) adding a suitable solvent selected from ketone solvents, ester solvents and ether solvents, followed by a hydrocarbon solvent to the reaction mixture,
 d) heating the reaction mixture,
 e) stirring the reaction mixture,
 f) filtering the solid and then dried to get amorphous Dabigatran etexilate (−)-camphor sulfonate.

A preferred embodiment of the present invention is to provide a process for the preparation of an amorphous Dabigatran etexilate (−)-camphor sulfonate, comprising of:
 a) Reacting Dabigatran etexilate with (−)-camphor sulfonic acid in acetone,
 b) concentrating the reaction mixture,
 c) adding acetone followed by n-heptane to the reaction mixture,
 d) heating the reaction mixture,
 e) stirring the reaction mixture,
 f) filtering the solid and then dried to get amorphous Dabigatran etexilate (−)-camphor sulfonate.

In seventh, eighth and ninth aspects of the present invention (−)-camphor sulfonic acid can be replaced with (+)-camphor sulfonic acid to provide its corresponding (+)-camphor sulfonate salt.

The tenth aspect of the present invention relates to novel polymorph of Dabigatran etexilate oxalate herein designated as crystalline form-S. The crystalline form-S of Dabigatran etexilate oxalate characterized by its powder X-ray diffraction pattern having peaks at 3.9, 7.5, 7.8, 11.9, 18.2, 20.0 and 27.0±0.2 degrees of 2θ values. The crystalline form-S of Dabigatran etexilate oxalate, further characterized by the PXRD pattern as illustrated in figure-9.

Further, the tenth aspect of the present invention also provides a process for the preparation of crystalline form-S of Dabigatran etexilate oxalate, comprising of:
a) Dissolving dabigatran etexilate compound of formula-1 in a suitable ketone solvent,
b) adding a solution of oxalic acid dissolved in a suitable ketone solvent,
c) stirring the reaction mixture,
d) filtering the solid and then dried to get crystalline form-S of Dabigatran etexilate oxalate.

A preferred embodiment of the present invention provides a process for the preparation of crystalline form-S of Dabigatran etexilate oxalate, comprising of:
a) Dissolving dabigatran etexilate compound of formula-1 in acetone,
b) adding a solution of oxalic acid dissolved in acetone,
c) stirring the reaction mixture,
d) filtering the solid and then dried to get crystalline form-S of Dabigatran etexilate oxalate.

The eleventh aspect of the present invention relates to a novel polymorph of Dabigatran etexilate fumarate herein designated as crystalline form-N. The crystalline form-N of Dabigatran etexilate fumarate is characterized by its powder-X-ray diffraction pattern having peaks at 4.9 and 5.2±0.2 degrees of 2θ values. The crystalline form-N of Dabigatran etexilate fumarate is further characterized by PXRD pattern as illustrated in figure-10.

Further, the eleventh aspect of the present invention also provides a process for the preparation of crystalline form-N of Dabigatran etexilate fumarate, comprising of:
a) Dissolving dabigatran etexilate compound of formula-1 in a suitable ketone solvent,
b) adding a solution of fumaric acid dissolved in a suitable ketone solvent,
c) stirring the reaction mixture,
d) filtering the solid and then dried to get crystalline form-N of Dabigatran etexilate fumarate.

A preferred embodiment of the present invention provides a process for the preparation of crystalline form-N of Dabigatran etexilate fumarate, comprising of:
a) Dissolving dabigatran etexilate compound of formula-1 in acetone,
b) adding a solution of fumaric acid dissolved in acetone,
c) stirring the reaction mixture,
d) filtering the solid and then dried to get crystalline form-N of Dabigatran etexilate fumarate.

The twelfth aspect of the present invention provides a process for the preparation of crystalline form-I of Dabigatran etexilate mesylate compound of formula-1a, comprising of:
a) Dissolving dabigatran etexilate in acetonitrile,
b) adding a solution of methane sulfonic acid dissolved in acetonitrile,
c) stirring the reaction mixture,
d) filtering the precipitated solid and then dried to get crystalline form-I of Dabigatran etexilate mesylate compound of formula-1a.

The PXRD analysis of crystalline compounds and amorphous compounds of the present invention was carried out using BRUKER/AXS X-ray diffractometer using CuKα radiation of wavelength 1.5406 A° and continuous scan speed of 0.03°/min.

Differential scanning calorimetric (DSC) analysis was performed on a Q10 V9.6 Build 290 calorimeter with closed aluminium pans, heating the samples from 40 to 300° C. in a dry nitrogen atmosphere at a rate of 10° C./min.

Dabigatran etexilate mesylate compound of formula-1a produced by the present invention can be further micronized or milled to get the desired particle size to achieve desired solubility profile based on different forms of pharmaceutical composition requirements. Techniques that may be used for particle size reduction include, but not limited to ball mills, roller and hammer mills and jet mills. Milling or micronization may be performed before drying or after the completion of drying of the product.

HPLC Analysis of Innovator Tablet

The present inventors has also analyzed the Pradaxa 110 mg tablet having Lot no: 808809 and compared with dabigatran etexilate mesylate obtained from the present invention and found that, the impurity profile of both the products are similar to each other i.e., amide impurity, despyridyl ethyl ester etc. are well present even in Pradaxa tablet. Henceforth, we can presume that these impurities are known from the art.

Amide Impurity: 0.31%; Despyridyl ethyl ester: 0.10%; Deshexyl Impurity: 0.08%.

HPLC Method of Analysis:
a) Dabigatran Etexilate (Formula-1) and Dabigatran Etexilate Mesylate (Formula-1a):

Apparatus: A liquid chromatographic system is to be equipped with variable wavelength UV-detector; Column: Zorbax Eclipse XDB C18, 100×4.6 mm, 3.5 μm or Equivalent; Flow Rate:1.0 mL/min; Wavelength: 300 nm; Column temperature: 25° C.; Injection volume: 5 μL; Run time: 50 minutes; Auto sampler temperature: 5° C.; Buffer: Dissolve 0.63 gm of Ammonium formate in 1000 mL of Milli-Q-Water and mix well. Adjust its pH to 8.2 with Ammonia and filtered through 0.22 μm nylon membrane and degas it. Mobile phase-A: Buffer; Mobile phase-B: Acetonitrile: Water (80:20) v/v; Diluent: N,N-Dimethylformamide; Needle wash: Diluent; Elution: Gradient.

b) Ethyl 3-(2-(4-cyanophenylamino)methyl)-1-methyl-N-(pyridin-2-yl)-1H-benzo[d]imidazole-5-carboxamido)propanoate methanesulfonate (Formula-10)

Apparatus: A liquid chromatograph is equipped with variable wavelength UV-Detector; Column: Zorbax SB CN 150× 4.6 mm, 5 μm (or) Equivalent (Make: Agilent and PNo: 883975-905); Flow Rate: 1.0 mL/min; Column temperature: 25° C.; Wave length: 290 nm; Injection volume: 5 μL; Run time: 60 minutes; Elution: Gradient; Diluent: Water: Acetonitrile (70:30) v/v; Needle wash: Diluent; Buffer: Weigh accurately about 2 g of 1-Octane sulphonic acid sodium salt anhydrous and add 5 mL of Ortho phosphoric acid in 1000 mL of Milli-Q-Water and mix well, filter this solution through 0.22 μm nylon membrane and sonicate to degas; Mobile Phase-A: Buffer(100%); Mobile Phase-B: Acetonitrile: Methanol (90:10) v/v.

c) Ethyl 3-(2-((4-carbamimidoylphenylamino)methyl)-1-methyl-N-(pyridin-2-yl)-1H-benzo[d]imidazole-5-carboxamido)propanoate methanesulfonate (Formula-11)

Apparatus: A liquid chromatographic system is to be equipped with variable wavelength UV-Detector and Integrator; Column: Zodiac C18 250×4.6 mm, 5 μm (or) equivalent (Make: Zodiac and PNo. ZLS.C18.46.250.0510); Flow Rate: 1.0 mL/min; Wavelength: 290 nm; Column temperature: 25° C.; Injection Volume: 54; Run time: 55 min; Elution: Gradient; Buffer: Take 5 mL of Ortho phosphoric acid(85%) and 2 g of 1-Octane sulfonic acid sodium salt anhydrous in 1000 mL of Milli-Q-water and adjust its pH to 2.5 with Triethyl amine filter, through 0.22 μM Nylon membrane filter paper and sonicate to degas it; Mobile Phase-A: Buffer(100%) Mobile Phase-B: Acetonitrile: Water (90:10) v/v; Diluent: Water: Acetonitrile (80:20) v/v.

Morphology: Method of Analysis:

Samples were mounted on aluminium stubs using double adhesive tape, coated with gold using HUS-5 GB vacuum evaporation and observed in Hitachi S-3000 N SEM at an acceleration voltage of 10 KV.

Following are the impurities observed during the preparation of Dabigatran etexilate mesylate.

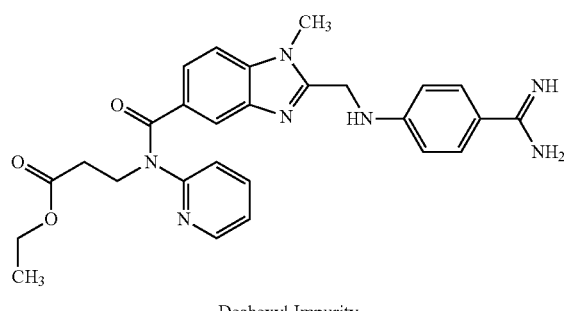

Deshexyl Impurity

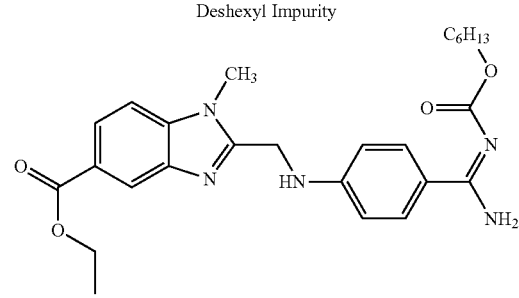

Despyridyl Ethyl Ester

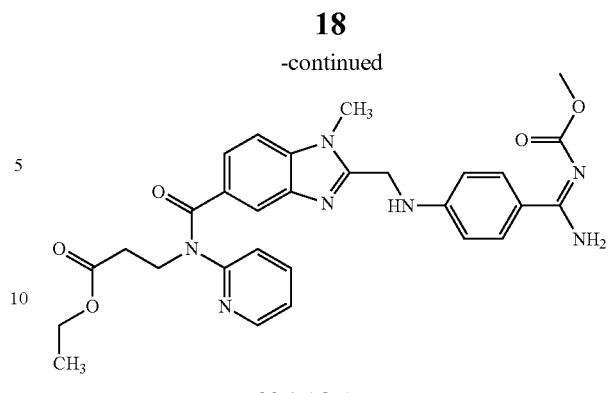

Methyl Carbamate

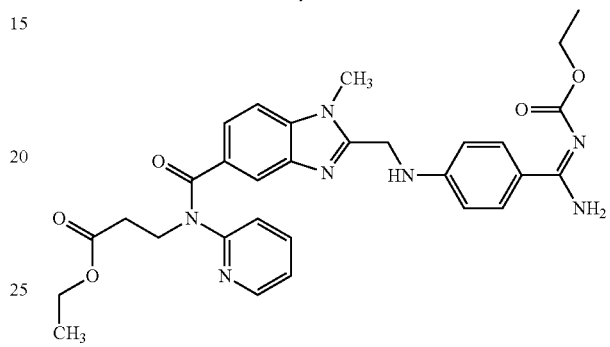

Ethyl Carbamate

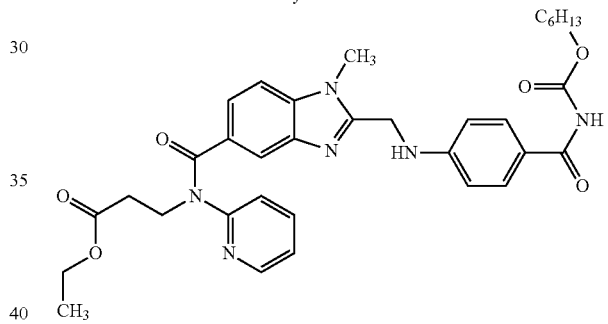

Amide Impurity

The present invention is schematically represented as follows:

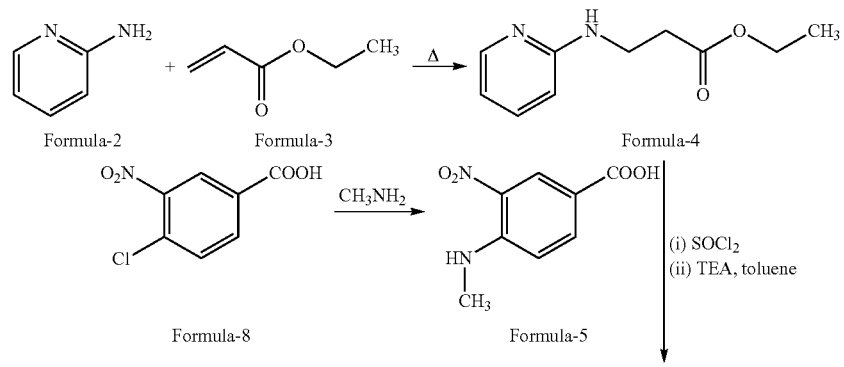

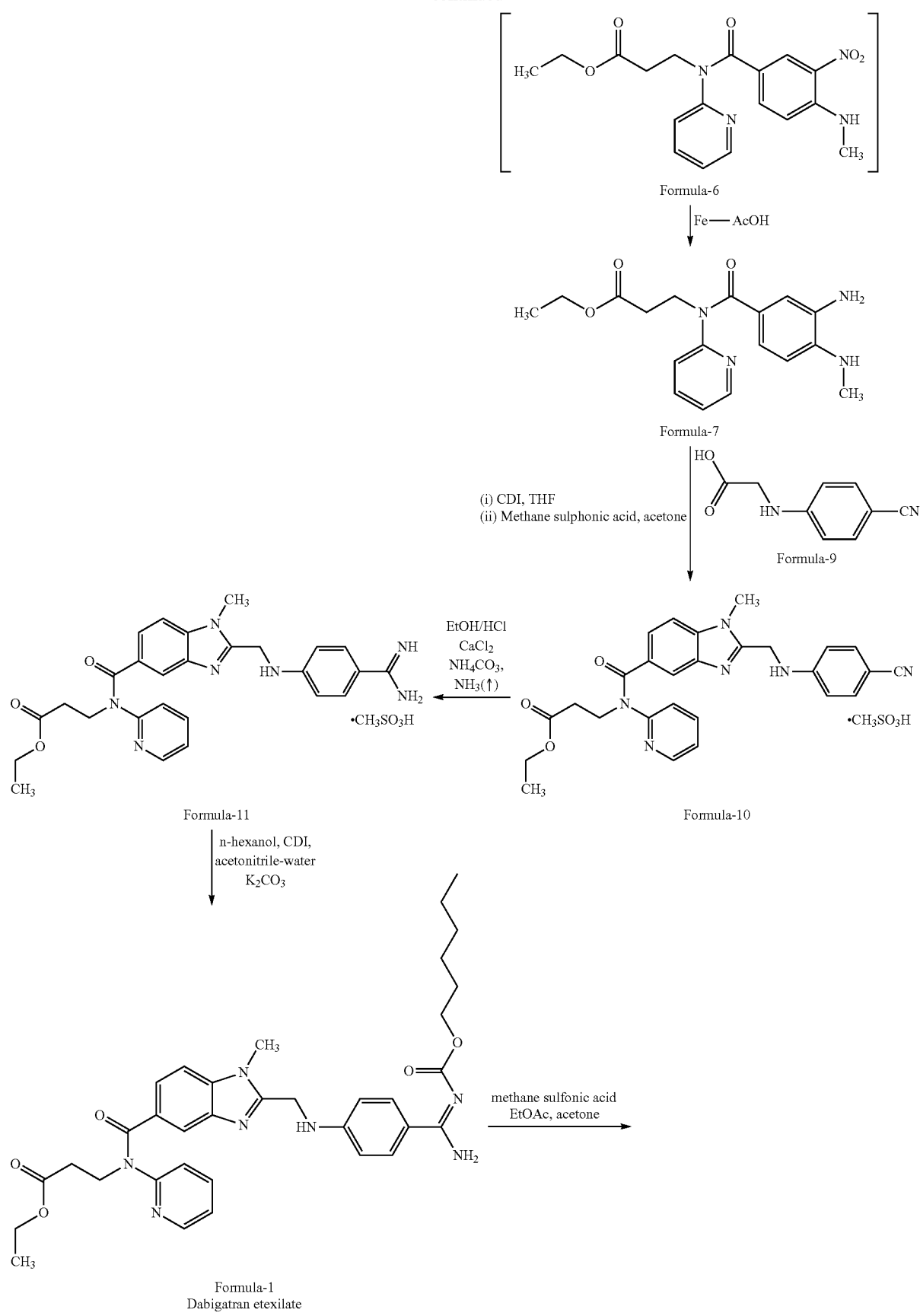

-continued

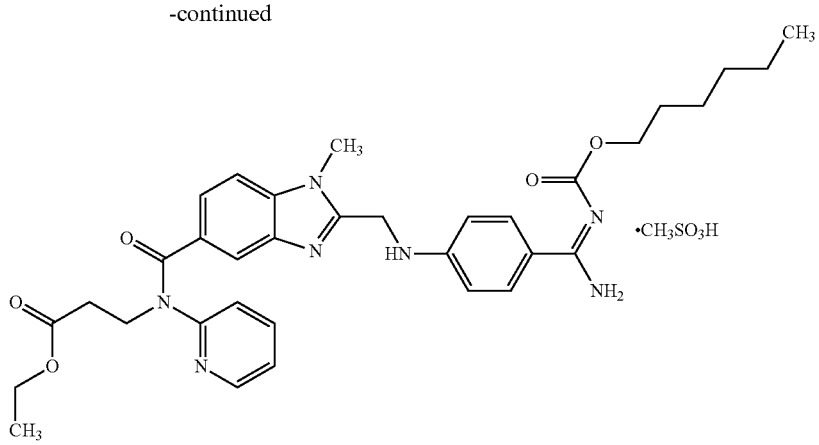

Formula-1a
Dabigatran etexilate Mesylate

The process described in the present invention was demonstrated in examples illustrated below. These examples are provided as illustration only and therefore should not be construed as limitation of the scope of the invention.

EXAMPLES

Example-1

Preparation of ethyl 3-(pyridin-2-ylamino)propanoate (Formula-4)

A mixture of 2-aminopyridine (100 g) and ethyl acrylate (234 g) was heated to 95-100° C. and then stirred for 75 hours at the same temperature. After completion of the reaction, the reaction mixture was cooled to 25-35° C. Ethyl acetate was added to the reaction mixture and treating the reaction mixture with hydrochloric acid followed by ammonia. Both the organic and aqueous layers were separated, the organic layer was washed with sodium chloride solution and then distilled off the solvent completely from the organic layer to get title compound as a residue. The obtained residue was isolated from pet.ether to provide crude title compound. The obtained compound was further purified by column chromatography using pet.ether and ethyl acetate. The obtained pure compound was further recrystallized using pet.ether. Yield: 75 g; MP: 52-54° C.

Example-2

Preparation of ethyl 3-(pyridin-2-ylamino)propanoate (Formula-4)

A mixture of 2-aminopyridine (200 g) and ethyl acrylate (468 g) was heated to 90-100° C. and then stirred for 50 hours at the same temperature. After completion of the reaction, the reaction mixture was cooled to 25-35° C. Ethyl acetate was added to the reaction mixture and treating the reaction mixture with hydrochloric acid, followed by ammonia. Both the organic and aqueous layers were separated, the organic layer was washed with sodium chloride solution and then distilled off the solvent completely from the organic layer to get title compound as a residue. Yield: 295 grams.

Example-3

Preparation of 4-(methylamino)-3-nitrobenzoic acid (Formula-5)

A mixture of 4-chloro-3-nitrobenzoic acid compound of formula-8 (200 g) and methyl amine (660 ml) was taken into autoclave and heated to 85-90° C. and stirred for 5 hours under pressure of 2.0-2.5 kg. After completion of the reaction, the reaction mixture was cooled to 25-35° C. Quenched the reaction mixture with water and then acidified with hydrochloric acid. Filtered the precipitated solid and then dried to get title compound.
Yield: 190 g.

Example-4

Preparation of 4-(methylamino)-3-nitrobenzoic acid (Formula-5)

A mixture of 4-chloro-3-nitrobenzoic acid compound of formula-8 (200 g) and 40% solution of methyl amine (660 ml) was taken into autoclave and heated to 85-90° C. and stirred for 5 hours. After completion of the reaction, the reaction mixture was cooled to 25-35° C. Water was added to the reaction mixture and acidified with hydrochloric acid. Filtered the precipitated solid, washed with water and then dried to get title compound.
Yield: 195 g.

Example-5

Preparation of ethyl 3-(4-(methylamino)-3-nitro-N-(pyridin-2-yl)benzamido) propanoate (Formula-6)

A mixture of 4-(methylamino)-3-nitrobenzoic acid compound of formula-5 (151.4 g), thionyl chloride (64 ml), dimethyl formamide (5 ml) and toluene (400 ml) was heated to 65-75° C. and stirred for 2 hours. After completion of the reaction, the solvent from the reaction mixture was completely distilled off under reduced pressure and followed by co-distillation with toluene to get the corresponding acid chloride compound as a residue. Toluene (300 ml) was added to the obtained residue. Triethyl amine (157.5 ml), followed by a solution of ethyl 3-(pyridin-2-ylamino)propanoate compound of formula-4 (50 g) and toluene (200 ml) was added to the reaction mixture and stirred for 3 hours at 20-30° C. Filtered the unwanted solid, the filtrate was washed with sodium bicarbonate solution followed by water and sodium chloride solution. The organic layer was concentrated to get title compound. Yield: 162 g.

Example-6

Preparation of ethyl 3-(3-amino-4-(methylamino)-N-(pyridin-2-yl)benzamido) propanoate (Formula-7)

Step-(a): Preparation of ethyl 3-(4-(methylamino)-3-nitro-N-(pyridin-2-yl)benzamido) propanoate (Formula-6)

A mixture of 4-(methylamino)-3-nitrobenzoic acid compound of formula-5 (453.12 g) and toluene (400 ml) was heated to reflux temperature and water was collected by azeotropic distillation for about 3 hours. Dimethyl formamide (15 ml) and thionyl chloride (403.0 g) were added to the reaction mixture. The reaction mixture was heated to 65-75° C. and stirred for 2 hours at the same temperature. After completion of the reaction, the solvent from the reaction mixture was completely distilled off under reduced pressure under nitrogen atmosphere, followed by co-distilled with toluene to get the corresponding acid chloride compound as a residue. Toluene (900 ml), triethylamine (474.1 ml) were added to the obtained residue and stirred for 15 minutes. A solution of ethyl 3-(pyridin-2-ylamino) propanoate compound of formula-4 (300 g) and toluene (600 ml) was added to the reaction mixture at 20-30° C. and stirred for 3 hours at 20-30° C. Filtered the unwanted solid, the filtrate was washed with sodium bicarbonate solution followed by water and sodium chloride solution. The organic layer was distilled off completely to get title compound as a residue.

Step-(b): Preparation of ethyl 3-(3-amino-4-(methylamino)-N-(pyridin-2-yl)benzamido) propanoate (Formula-7)

Tetrahydrofuran (600 ml) and water (600 ml) were added to the compound obtained in step-(a), followed by Iron powder (343.7 g) and the reaction mixture was heated to 60-70° C. Acetic acid (277.4 g) was added slowly to the reaction mixture at 60-70° C. over a period of 2 hours. After completion of the reaction, the reaction mixture was cooled to 25-35° C. Dichloromethane and water were added to the reaction mixture and stirred for 20 minutes. Filtered the reaction mixture through the hy-flow bed, washed the bed with dichloromethane. The organic and aqueous layers were separated from the filtrate; the organic layer was washed with sodium bicarbonate solution, followed by sodium chloride solution. Distilled off the solvent from the organic layer and then co-distilled with ethyl acetate to get crude compound. The obtained compound was recrystallized from ethyl acetate. Yield: 360 g.

Example-7

Preparation of ethyl 3-(3-amino-4-(methylamino)-N-(pyridin-2-yl)benzamido) propanoate (Formula-7)

Iron powder (35.9 g) was added to a mixture of ethyl 3-(4-(methylamino)-3-nitro-N-(pyridin-2-yl)benzamido) propanoate compound of formula-6 (60 g), tetrahydrofuran (63 ml) and water (63 ml) and the reaction mixture was heated to reflux temperature. Acetic acid (29.02 g) was slowly added to the reaction mixture at the same temperature over a period of 2 hours. After completion of the reaction, the reaction mixture was cooled to 25-35° C. and dichloromethane and water were added to the reaction mixture. Filtered the reaction mixture through hyflow bed, both organic and aqueous layers were separated from the filtrate and the organic layer was washed with sodium bicarbonate solution followed by sodium chloride solution. Distilled off the solvent completely from the organic layer and then co-distilled with ethyl acetate to obtain the title compound. The obtained compound was recrystallized from ethyl acetate.
Yield: 36.0 g; MR: 103-108° C.

Example-8

Preparation of ethyl 3-(3-amino-4-(methylamino)-N-(pyridin-2-yl)benzamido) propanoate (Formula-7)

Iron powder (35.9 g) was added to a mixture of ethyl 3-(4-(methylamino)-3-nitro-N-(pyridin-2-yl)benzamido) propanoate compound of formula-6 (60 g), tetrahydrofuran (63 ml) and water (63 ml) and heated the reaction mixture to reflux temperature. Hydrochloric acid (17.6 g) was slowly added to the reaction mixture at the same temperature over a period of 2 hours. After completion of the reaction, the reaction mixture was cooled to 25-35° C. and dichloromethane and water were added. Filtered the reaction mixture through hyflow bed, both organic and aqueous layers were separated from the filtrate and the organic layer was washed with sodium bicarbonate solution followed by sodium chloride solution. Distilled off the solvent completely from the organic layer and then co-distilled with ethyl acetate to obtain the title compound. The obtained compound was recrystallized from ethyl acetate. Yield: 61.0 g; MR: 103-108° C.

Example-9

Preparation of 2-(4-cyanophenylamino)acetic acid (Formula-9)

Sodium mono chloroacetate (197.42 g), followed by potassium iodide (5 g) and tetrabutyl ammonium bromide (2.5 g) were added to a mixture of 4-aminobenzonitrile (100 g), water (1000 ml) and sodium bicarbonate (42.71 g). The reaction mixture was heated to 85-90° C. and stirred for 24 hours. The reaction mixture was cooled to 25-30° C. and treated with ammonia followed by hydrochloric acid. Filtered the solid, washed with water and then dried to get title compound.
Yield: 120 g.

Example-10

Preparation of ethyl 3-(2-((4-cyanophenylamino)methyl)-1-methyl-N-(pyridin-2-yl)-1H-benzo[d]imidazole-5-carboxamido)propanoate mesylate (Formula-10)

A mixture of 2-(4-cyanophenylamino)acetic acid compound of formula-9 (64.32 g) and toluene (400 ml) was heated to reflux and water was collected by azeotropic distillation for 2 hours. Toluene was distilled off completely from the reaction mixture. The reaction mixture was cooled to 10-20° C. Tetrahydrofuran (1000 ml), followed by N,N-carbonyldiimidazole (71.03 g) were added to the reaction mixture at 10-20° C. under nitrogen atmosphere and then stirred for 60 minutes at 10-20° C. Ethyl 3-(3-amino-4-(methylamino)-N-(pyridin-2-yl)benzamido) propanoate compound of formula-7 (100 g) was added slowly to the reaction mixture and the temperature of the reaction mixture was raised to 20-30° C. and then stirred for 16 hours. After completion of the reaction, distilled off the solvent completely from the reaction mixture under reduced pressure. Acetic acid (600 ml) was added to the reaction mixture, heated the reaction mixture to 55-65° C. and then stirred for 7 hours. After completion of the reaction, the reaction mixture was cooled to 20-30° C. Water, followed by dichloromethane were added to the reaction mixture. The organic and aqueous layers were separated, the organic layer was washed with water followed by sodium chloride solution. The solvent from the organic layer was completely distilled off under reduced pressure and then co-distilled with acetone. The obtained compound was dissolved in acetone (700 ml) and then cooled to −5 to +5° C. and stirred for 30 minutes. Methane sulfonic acid (14.2 ml) was added slowly to the reaction mixture at −5 to +5° C. and stirred for 3 hours. Filtered the precipitated solid, washed with acetone. Acetone (500 ml) was added to the obtained solid; the reaction mixture was heated to 45-55° C. and stirred for 60 minutes. The reaction mixture was cooled to −5 to +5° C. and stirred for 2 hours at −5 to +5° C. Filtered the solid, washed with the mixture of dimethylformamide and acetone and then dried to get title compound.

Yield: 115 g; MR: 188-192° C.

The PXRD, IR and DSC of the obtained crystalline compound is illustrated in figure-1, figure-2 and figure-3. The obtained crystalline solid of compound of formula-10 herein designated as "crystalline form-M".

Example-11

Purification of ethyl 3-(2-((4-cyanophenylamino) methyl)-1-methyl-N-(pyridin-2-yl)-1H-benzo[d] imidazole-5-carboxamido)propanoate mesylate (Formula-10)

Dimethylformamide (150 ml) and acetone (500 ml) were added to the wet solid of ethyl 3-(2-((4-cyanophenylamino) methyl)-1-methyl-N-(pyridin-2-yl)-1H-benzo[d]imidazole-5-carboxamido) propanoate mesylate, obtained in example-10 and the reaction mixture was heated to 65-75° C. and stirred for 60 minutes. The reaction mixture was cooled to −5 to +5° C. and stirred for 2 hours at the same temperature. Filtered the solid, washed with cyclohexane followed by mixture of dimethylformamide and acetone then dried to get title compound.

Yield: 115 g; MR: 188-192° C.; Purity by HPLC: 99.3%.

Example-12

Preparation of ethyl 3-(2-((4-carbamimidoylphenylamino)methyl)-1-methyl-N-(pyridin-2-yl)-1H-benzo [d]imidazole-5-carboxamido)propanoate mesylate (Formula-11)

Hydrochloric acid gas was slowly passed into a mixture of calcium chloride dihydrate (12.5 g) and ethanol (150 ml) at −15 to −5° C. for a period of 3 hours. Ethyl 3-(2-((4-cyanophenylamino)methyl)-1-methyl-N-(pyridin-2-yl)-1H-benzo[d]imidazole-5-carboxamido)propanoate mesylate compound of formula-10 (50 g) was added to the reaction mixture and hydrochloric acid gas was again purged into the reaction mixture at −15 to 5° C. The temperature of the reaction mixture was raised to 25-35° C. and stirred for 10 hours. The reaction mixture was added to the solution containing ammonium carbonate (50 g), ammonia gas and ethanol (250 ml) at −35 to −25° C. and stirred for 20 minutes. The temperature of the reaction mixture was raised to 25-35° C. and stirred for 3 hours. The reaction mixture was heated to reflux temperature and stirred for 2 hours. Filtered the unwanted solid and distilled off the solvent completely from the filtrate to obtain crude title compound. The obtained crude compound was dissolved in ethanol (50 ml) and ethyl acetate (250 ml) was added to the reaction mixture and stirred for 12 hours. Filtered the precipitated solid and then dried to get pure title compound.

Yield: 46 g; MR: 198-202° C. Purity by HPLC: 83%.

The PXRD, IR and DSC of the obtained crystalline compound is illustrated in figure-4, figure-5 and figure-6. The obtained crystalline solid of compound of formula-11 herein designated as crystalline form-N.

Example-13

Preparation of Dabigatran etexilate (Formula-1)

n-hexanol (30.8 g) was added to a solution of N, N-carbonyldiimidazole (61.15 g) and dichloromethane (360 ml) at 15-25° C. and stirred for 3 hours. The organic layer was washed with water followed by sodium chloride solution. Distilled off the solvent from the organic layer completely under reduced pressure to get amide compound. Acetonitrile (157.5 ml) was added to the obtained amide compound. This was added to a mixture of ethyl 3-(2-((4-carbamimidoylphenylamino)methyl)-1-methyl-N-(pyridin-2-yl)-1H-benzo[d] imidazole-5-carboxamido)propanoate mesylate compound of formula-11 (90 g), potassium carbonate (62.5 g), acetonitrile (378 ml) and water (252 ml) at 25-35° C. The reaction mixture was heated to 40-50° C. and stirred for 8 hours. After completion of the reaction, both the organic and aqueous layers were separated; the organic layer was cooled to −5 to +5° C. and stirred for 2 hours. Filtered the precipitated solid washed with acetonitrile and water. The obtained compound was dissolved in a mixture of acetone (270 ml) and acetonitrile (270 ml) at 45-50° C. Cooled the reaction mixture to 25-30° C. and water (360 ml) was added to it. Filtered the obtained solid and dissolved in the mixture of dichloromethane and sodium chloride solution at 35-40° C. Both the organic and aqueous layers were separated; the organic layer was distilled under reduced pressure and then co-distilled with ethyl acetate. The obtained crude compound was dissolved in ethyl acetate (540 ml) by heating it to 70-80° C. and stirred for 30 minutes. Filtered the reaction mixture, the filtrate was cooled to 35-45° C. and ethanol (8 ml) was added to the reaction mixture. The reaction mixture was again cooled to 25-35° C. and stirred for 3 hours. Filtered the precipitated solid and then dried to get pure title compound.

Yield: 44 g; MR: 128-131° C. Purity by HPLC: 99.63%.

Example-14

Preparation of Dabigatran etexilate Mesylate (Formula-1a)

Dabigatran etexilate compound of formula-1 (50 g) was dissolved in acetone (500 ml) at 50-60° C. Filtered the reaction mixture and washed with hot acetonitrile. The filtrate was cooled to 30-40° C. A solution of methane sulfonic acid (5.06 ml) and ethyl acetate (200 ml) was slowly added to the reaction mixture at 26-32° C. and stirred for 4 hours at 25-35° C. Filtered the precipitated solid, washed with ethyl acetate and then dried to get title compound.

Yield: 54 g; MR: 179-181° C.;

Purity by HPLC: 99.8%; Deshexyl Impurity: 0.01%; Methyl carbomate Impurity: 0.02%; Ethyl carbomate: 0.02%; Amide Impurity: 0.01%; Despyridyl ethyl ester Impurity: 0.05%; Unknown Impurity: 0.05%;

Particle size distribution: D10: 10.11 μm; D50: 51.88 μm; D90: 112.41 μm; Bulk Density: 0.32 g/ml; Tapped Density: 0.44 g/ml.

The PXRD of the obtained compound matches with the crystalline form-I of Dabigatran etexilate mesylate of WO2005028468.

Example-15

Preparation of crystalline form-I of Dabigatran etexilate mesylate (Formula-1a) from tetrahydrofuran Methane sulfonic acid (1.5 g) was slowly added to a mixture of Dabigatran etexilate (10 g) and tetrahydrofuran (120 ml) at 25-30° C. and stirred for 5 hours. Filtered the precipitated solid, washed with tetrahydrofuran and then dried to get crystalline form-I of Dabigatran etexilate mesylate.

Yield: 11 g; MR: 176-180° C.

The PXRD of the obtained compound matches with the crystalline form-I of Dabigatran etexilate mesylate of WO2005028468.

Example-16

Preparation of crystalline form-I of Dabigatran etexilate mesylate (Formula-1a) from acetonitrile A mixture of Dabigatran etexilate (10 g) and acetonitrile (100 ml) was heated to 50-60° C. Filtered the reaction mixture through hyflow bed and washed with acetonitrile. Methane sulfonic acid (1.5 g) was slowly added to the obtained filtrate at 25-30° C. and stirred for 5 hours. Filtered the precipitated solid, washed with acetonitrile and then dried to get crystalline form-I of Dabigatran etexilate mesylate.

Yield: 10.6 g; MR: 178-181° C.

The PXRD of the obtained compound matches with the crystalline form-I of Dabigatran etexilate mesylate of WO2005028468.

Example-17

Preparation of crystalline form-M of Dabigatran etexilate (−)-camphor sulfonate salt A mixture of Dabigatran etexilate compound of formula-1 (50 g) and acetone (250 ml) was heated to 40-50° C. The reaction mixture was cooled to 25-35° C.; (−)-camphor sulfonic acid (20.18 g) was added to it and stirred for 3 hours under nitrogen atmosphere. The solvent from the reaction mixture was completely distilled off under reduced pressure. Ethanol (50 ml) was added to the obtained crude at 35-40° C. and cooled to 25-35° C. Methyl tertiary butyl ether (500 ml) was slowly added to the reaction mixture at 25-35° C. and stirred for 12 hours. Filtered the precipitated solid, washed with methyl tertiary butyl ether and then dried to get crystalline form-M of title compound. Yield: 52 g; MR: 158-160° C.

The PXRD of the obtained compound is illustrated in figure-7.

Example-18

Preparation of amorphous Dabigatran etexilate (−)-camphor sulfonate salt

A mixture of Dabigatran etexilate compound of formula-1 (10 g) and acetone (50 ml) was heated to 40-50° C. The reaction mixture was cooled to 25-35° C. (−)-camphor sulfonic acid (4.09 g) was added to it and stirred for 3 hours at 25-35° C. The reaction mixture was concentrated to 10 ml and then cooled to 25-35° C. Acetone (5 ml) and followed by n-heptane (100 ml) were added to the reaction mixture at 25-35° C. and stirred for 3 hours at the same temperature. The reaction mixture was heated to 50-55° C. and stirred for 10 hours at the same temperature. Filtered the precipitated solid and then dried to get amorphous Dabigatran etexilate (−)-camphor sulfonate.

Yield: 12 g; MR: 64-66° C.

The PXRD of the obtained compound is illustrated in figure-8.

Example-19

Preparation of crystalline form-S of Dabigatran etexilate oxalate

Dabigatran etexilate (10 g) was dissolved in acetone (100 ml) at 25-35° C. A solution of oxalic acid (2.41 g) and acetone (25 ml) was added to the reaction mixture at 25-35° C. and stirred for 5 hours at the same temperature. Filtered the precipitated solid and then dried to get crystalline form-S of Dabigatran etexilate oxalate.

Yield: 10.96 g; MR: 158-160° C.

The PXRD of the obtained compound is illustrated in figure-9.

Example-20

Preparation of crystalline form-N of Dabigatran etexilate fumarate

Dabigatran etexilate (10 g) was dissolved in acetone (100 ml) at 25-35° C. A solution of fumaric acid (2.22 g) dissolved in acetone (25 ml) was added to the reaction mixture at 25-35° C. and stirred for 5 hours at the same temperature. Filtered the precipitated solid and then dried to get crystalline form-N of Dabigatran etexilate fumarate.

Yield: 8.7 g; MR: 148-151° C.

The PXRD of the obtained compound is illustrated in figure-10.

Example-21

Preparation of ethyl 3-(2-((4-cyanophenylamino) methyl)-1-methyl-N-(pyridin-2-yl)-1H-benzo[d] imidazole-5-carboxamido)propanoate mesylate (Formula-10)

A mixture of 2-(4-cyanophenylamino)acetic acid compound of formula-9 (154.32 g) and toluene (800 ml) was heated to reflux temperature and water was collected by azeotropic distillation. Toluene was distilled off completely from the reaction mixture. The reaction mixture was cooled to 25-35° C.; tetrahydrofuran (600 ml) was added to the reaction mixture and stirred for 20 minutes. A solution of N, N-carbonyldiimidazole (161.04 g) and tetrahydrofuran (1000 ml) was added slowly to the above reaction mixture under nitrogen atmosphere and stirred for 3 hours at 25-35° C. to form an amide compound. A solution of ethyl 3-(3-amino-4-(methylamino)-N-(pyridin-2-yl)benzamido)propanoate compound of formula-7 (200 g) and tetrahydrofuran (1000 ml) was added to the above reaction mixture containing amide compound and stirred for 24 hours at 25-35° C. After completion of the reaction, distilled off the solvent completely from the reaction mixture under reduced pressure and then acetic acid (1200 ml) was added to the reaction mixture. The reaction mixture was heated to 55-65° C. and then stirred for 7 hours at 55-65° C. After completion of the reaction, the reaction mixture was cooled to 25-30° C. The reaction mixture was quenched with water and then extracted with dichloromethane. The dichloromethane layer was washed with water followed by sodium chloride solution. The organic layer was concentrated to get residue and then acetone (1200 ml) was added to the obtained residue. A solution of methane sulfonic acid (28.4 ml) and acetone (400 ml) was added to the reaction mixture at 0-10° C. and then stirred for 3 hours. Filtered the obtained solid and further purified by recrystallization from a mixture of dimethylformamide and acetone to get pure title compound.

Yield: 220 g; MR: 188-190° C.; purity by HPLC: 98%; 1H NMR (DMSO-d6, TMS as internal standard) δ: 1.09-1.13 (3H, t), 2.32 (3H, s), 2.67-2.72 (2H, t), 3.92 (3H, brs), 3.95-4.00 (2H, q), 4.19-4.24 (2H, t), 4.49 (1H, brs), 4.91 (2H, brs), 6.83-6.86 (2H, d), 7.05-7.08 (1H, d), 7.14-7.18 (1H, q), 7.38-7.41 (1H, d), 7.53-7.64 (4H, m), 7.78-7.80 (1H, d), 8.36-8.37 (1H, brd).

PXRD, IR spectrum and DSC thermogram of the obtained compound of formula-10 is illustrated in figure-1, figure-2 and figure-3 respectively.

Example-22

Preparation of ethyl 3-(2-((4-carbamimidoylphenylamino)methyl)-1-methyl-N-(pyridin-2-yl)-1H-benzo[d]imidazole-5-carboxamido)propanoate mesylate (Formula-11)

Hydrogen chloride gas was passed into a mixture of calcium chloride (125 g) and ethanol (1500 ml) at a temperature below 20° C. for a period of 30 minutes. The reaction mixture was cooled to −15 to −5° C. and stirred for 15 minutes. Ethyl 3-(2-((4-cyanophenylamino)methyl)-1-methyl-N-(pyridin-2-yl)-1H-benzo[d]imidazole-5-carboxamido)propanoate mesylate compound of formula-10 (500 g) was added to the reaction mixture. Hydrogen chloride gas was slowly purged into the reaction mixture for a period of 3 hours. The temperature of the reaction mixture was raised to 25-35° C. and stirred for 10 hours. After completion of the reaction, expell the hydrogen chloride gas present in the reaction mixture under nitrogen atmosphere. Ethanol (2500 ml), followed by ammonium carbonate (2000 g) were added to the reaction mixture and stirred for 40 minutes at −30±5° C. The reaction mixture was cooled to 0-5° C. and ammonia gas was passed into the reaction mixture for 3 hours. The temperature of the reaction mixture was raised to 20-30° C. and stirred for 20 hours. After completion of the reaction, filtered the reaction mixture and the filtrate was concentrated to get title compound. Purity by HPLC: 80.61%;

The obtained compound was further dissolved in ethanol (500 ml); ethyl acetate (2500 ml) was added to the reaction mixture and then stirred for 2 hours at 25-35° C. to precipitate the solid. Filtered the solid and then dried to get pure title compound.

Yield: 380 g; MR: 198-202° C.; purity by HPLC: 95.6%; 1H NMR (DMSO-d6, TMS as internal standard) δ: 1.08-1.13 (3H, t), 2.32 (3H, s), 2.64-2.69 (2H, t), 3.76 (3H, brs), 3.92-3.99 (2H, m), 4.19-4.23 (2H, t), 4.63-4.64 (2H, brd), 6.84-6.90 (3H, m), 7.09-7.16 (2H, m), 7.38-7.41 (2H, m), 7.46 (1H, brs), 7.51-7.57 (1H, t), 7.62-7.65 (2H, brt), 8.37-8.38 (1H, brd), 8.51 (1H, brs), 8.82 (2H, brs).

The PXRD, IR spectrum and DSC thermogram of the obtained compound of formula-11 is illustrated in figure-4, figure-5 and figure-6 respectively.

Example-23

Preparation of 1-methyl-2-[N-[4-(N-n-hexyloxycarbonylamidino)phenyl]amino methyl]benzimidazol-5-yl-carboxylicacid-N-(2-pyridyl)-N-(2-ethoxycarbonylethyl) amide (Formula-1)

n-hexanol (38.76 g) was added to a solution of N,N-carbonyldiimidazole (76.95 g) in dichloromethane (400 ml) and stirred for 3 hours at 15-25° C. The dichloromethane was distilled under reduced pressure to form an amide compound. To a mixture of acetonitrile (420 ml), water (280 ml) and ethyl 3-(2-((4-carbamimidoylphenylamino)methyl)-1-methyl-N-(pyridin-2-yl)-1H-benzo[d]imidazole-5-carboxamido) propanoate mesylate compound of formula-11 (100 g), added potassium carbonate (128.7 g) at 25-35° C. and stirred for 15 minutes. To this reaction mixture, a solution of obtained amide compound in acetonitrile (150 ml) was added at 25-35° C. and stirred for 24 hours. After completion of the reaction, filtered the solid and purified from ethyl acetate (500 ml) to get title compound.

Yield: 68 grams; MR: 128-131° C.; purity by HPLC: 99.6%.

We claim:

1. A process for preparing the compound of Formula-1,

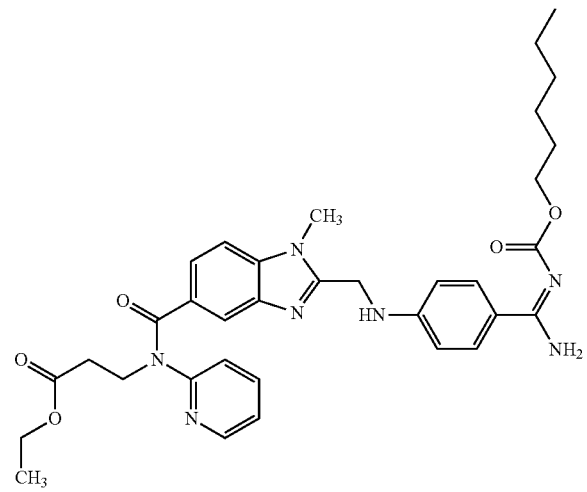

Formula-1 or a pharmaceutically acceptable salt thereof, the process comprising:
a) reacting 2-aminopyridine with ethyl acrylate at a temperature of 95-100° C. to prepare the compound of Formula-4,

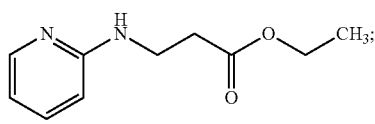

Formula-4 b) reacting the compound of Formula-8

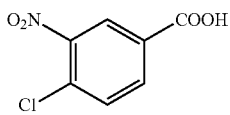

Formula-8 with methyl amine to provide the compound of Formula-5,

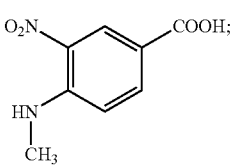

Formula-5 c) condensing the compound of Formula-5 with the compound of Formula-4 obtained in step (a) in a solvent selected from hydrocarbon solvents, chloro solvents, ester solvents, polar aprotic solvents, ether solvents, alcoholic solvents, ketone solvents, nitrile solvents, nitro solvents or polar solvents, or mixtures thereof, to provide the compound of Formula-6,

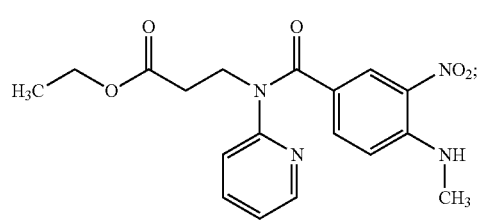

Formula-6 d) reducing the compound of Formula-6 in-situ with a reducing agent selected from Fe-acetic acid or Fe-hydrochloric acid in a solvent selected from hydrocarbon solvents, chloro solvents, ester solvents, polar aprotic solvents, ether solvents, alcoholic solvents, ketone solvents, nitrile solvents, nitro solvents or polar solvents, or mixtures thereof, to provide the compound of Formula-7,

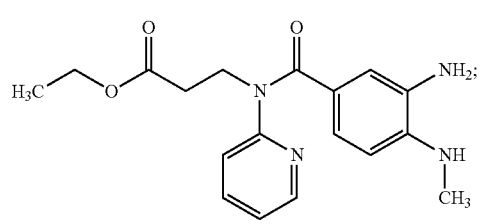

Formula-7 e) reacting the compound of Formula-7 with the compound of Formula-9

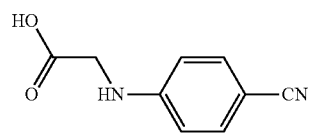

Formula-9 in presence of a condensing agent selected from pivaloyl chloride, polyphosphoric acid, carbodiimides, alkyl or aryl chloroformates, 3-hydroxy-3,4-dihydro-1,2,3-benzotriazin-4-one, diethylphosphorocyanidate (DEPC), diphenylphosphoroazidate (DPPA), $P_2O_5$, 3-(diethoxyphosphoryloxy)-1,2,3-benzotriazine-4(3H)-one (DEPBT) or N,N'-carbonyldiimidazole in a solvent selected from hydrocarbon solvents, chloro solvents, ester solvents, polar aprotic solvents, ether solvents, alcoholic solvents, ketone solvents, nitrile solvents, nitro solvents or polar solvents, or mixtures thereof, and reacting the obtained compound in-situ with methane sulfonic acid in a solvent selected from hydrocarbon solvents, chloro solvents, ester solvents, polar aprotic solvents, ether solvents, alcoholic solvents, ketone solvents, nitrile solvents, nitro solvents or polar solvents, or mixtures thereof, to provide the compound of Formula-10,

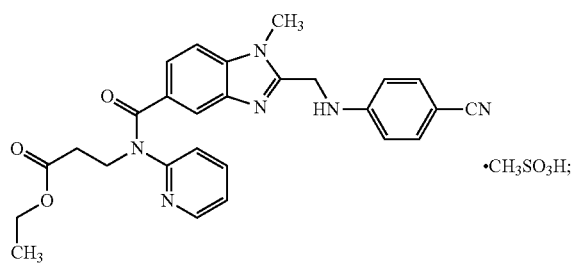

Formula-10 f) treating the compound of Formula-10 with an ammonia source selected from formamide, ammonium carbamate, ammonium formate, ammonium phosphate, ammonium acetate, ammonium fluoride, ammonium bromide, ammonium chloride, ammonium iodide, ammonium iodate, ammonium carbonate, ammonium citrate, ammonium chromate, ammonium dichromate, ammonium hydroxide, ammonium lactate, ammonium molybdate, ammonium nitrate, ammonium oxalate, ammonium sulfate, ammonium sulfide, ammonium tartrate, ammonium triflate, ammonium thiocyanate, ammonium dihydrogen phosphate, urea, methyl carbamate, ethyl carbamate, propyl carbamate or t-butte carbamate and/ or ammonia gas in presence of hydrogen chloride gas and Lewis acid in a solvent selected from hydrocarbon solvents, chloro solvents, ester solvents, polar aprotic solvents, ether solvents, alcoholic solvents, ketone solvents, nitrile solvents, nitro solvents or polar solvents, or mixtures thereof, to provide compound of Formula-11,

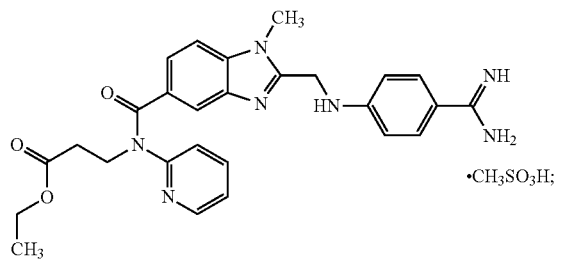

Formula-11

·CH₃SO₃H;

g) reacting n-hexanol and N,N-carbonyldiimidazole in a solvent selected from hydrocarbon solvents, chloro solvents, ester solvents, polar aprotic solvents, ether solvents, alcoholic solvents, ketone solvents, nitrile solvents, nitro solvents or polar solvents, or mixtures thereof, to provide an amide compound; and h) reacting the amide compound of step-(g) in-situ with the compound of Formula-11 in presence of a base selected from an inorganic base or an organic base or a mixture thereof in a solvent selected from hydrocarbon solvents, chloro solvents, ester solvents, polar aprotic solvents, ether solvents, alcoholic solvents, ketone solvents, nitrile solvents, nitro solvents or polar solvents, or mixtures thereof, to provide the compound of Formula-1.

2. The process according to claim 1, wherein:
in step-c), the solvent is selected from hydrocarbon solvents, ester solvents, ether solvents, polar aprotic solvents or mixtures thereof;
in step-d), the solvent is selected from ether solvents, hydrocarbon solvents, chloro solvents, ester solvents, alcoholic solvents, polar solvents, polar aprotic solvents or mixtures thereof;
in step-e), the condensing agent is selected from pivaloyl chloride, polyphosphoric acid, carbodiimides, alkyl or aryl chloroformates, 3 hydroxy-3,4-dihydro-1,2,3-benzotriazin-4-one, diethylphosphorocyanidate (DEPC), diphenylphosphoroazidate (DPPA), P₂O₅, or 3-(diethoxyphosphoryloxy)-1,2,3-benzotriazine-4(3H)-one (DEPBT); wherein the carbodiimides can be used optionally in combination with 1-hydroxybenzotriazole (HOBt), 1-hydroxy-7-azatriazole (HOAt), 1-hydroxy-1H-1,2,3-triazole-4-carboxylate (HOCt), N-hydroxy succinamide (HOSu), (2-(1H-benzotriazol-1-yl)-1,1,3,3-tetramethyluroniumtetrafluoroborate (TBTU), dimethylaminopyridine (DMAP); further wherein the alkyl or aryl chloroformates can be used optionally in combination with a base; the solvent used in the reaction of compound of Formula-7 and compound of Formula-9 is selected from ether solvents, hydrocarbon solvents, chloro solvents, ester solvents, ketone solvents, polar aprotic solvents or mixtures thereof; and the solvent for the mesylate formation is selected from ester solvents, alcoholic solvents, ether solvents, chloro solvents, ketone solvents or mixtures thereof;
in step-f), the suitable solvent is selected from alcoholic solvents, chloro solvents, ether solvents, ketone solvents or mixtures thereof; the Lewis acid is selected from aluminum chloride, aluminum bromide, boron trifluoride, boron trichloride, ferric chloride, tin(IV) chloride, calcium chloride or calcium chloride dihydrate; and the ammonia source is selected from formamide, ammonium carbamate, ammonium formate, ammonium phosphate, ammonium acetate, ammonium fluoride, ammonium bromide, ammonium chloride, ammonium iodide, ammonium iodate, ammonium carbonate, ammonium citrate, ammonium chromate, ammonium dichromate, ammonium hydroxide, ammonium lactate, ammonium molybdate, ammonium nitrate, ammonium oxalate, ammonium sulfate, ammonium sulfide, ammonium tartrate, ammonium triflate, ammonium thiocyanate, ammonium dihydrogen phosphate, urea, methyl carbamate, ethyl carbamate, propyl carbamate or t-butyl carbamate;
in step-g), the solvent is selected from chloro solvents, ester solvents, ether solvents, ketone solvents, polar aprotic solvents or nitrile solvents; and
in step-h), the solvent is organic solvent selected from polar aprotic solvents, ether solvents, ester solvents, nitrile solvents or ketone solvents or a mixture of water and organic solvent; and the base is selected from alkali metal carbonates and bicarbonates; and the reaction is carried out at a temperature ranging from 10-50° C.

3. The process according to claim 1, wherein:
i) the compound of Formula-6 is reduced in-situ with Fe-acetic acid in aqueous tetrahydrofuran in a solvent selected from hydrocarbon solvents, chloro solvents, ester solvents, polar aprotic solvents, ether solvents, alcoholic solvents, ketone solvents, nitrile solvents, nitro solvents or polar solvents, or mixtures thereof, to provide the compound of Formula-7;
ii) the compound of Formula-7 is reacted with the compound of Formula-9 in presence of N,N-carbonyldiimidazole in tetrahydrofuran, and the obtained compound is reacted in-situ with methane sulfonic acid in acetone to provide the compound of Formula-10;
iii) treating the compound of Formula-10 is treated with ammonium carbonate in presence of ammonia gas, hydrogen chloride gas and calcium chloride in ethanol to provide the compound of Formula-11; and
iv) the amide compound of step (g) is reacted in-situ with the compound of Formula-11 in presence of potassium carbonate in aqueous acetonitrile to provide the compound of Formula-1.

4. The process according to claim 1, wherein the solvent in step (d) is selected from ether solvents, hydrocarbon solvents, chloro solvents, ester solvents, alcoholic solvents, polar solvents, polar aprotic solvents or mixtures thereof.

5. The process according to claim 1, wherein the amount of Fe used in step (d) is in the range of 2-8 molar equivalents per 1 mole of compound of Formula-6; and the amount of acetic acid or hydrochloric acid used is in the range of 1-7 molar equivalents per 1 mole of compound of Formula-6.

6. The process according to claim 1, wherein the reaction in step (d) is carried out at a temperature ranging from 10° C. to 120° C.

7. The process according to claim 1, wherein the reducing agent in step (d) is Fe-acetic acid in aqueous tetrahydrofuran at reflux temperature.

8. The process according to claim 1, wherein the reducing agent in step (d) is Fe-hydrochloric acid in aqueous tetrahydrofuran at reflux temperature.

9. The process according to claim 1, wherein the condensing agent in a solvent in step (e) is N,N-carbonyldiimidazole in tetrahydrofuran and wherein the methane sulfonic acid is in acetone.

10. The process according to claim 1, wherein the reaction in step (f) is performed with ammonium carbonate in presence of ammonia gas, hydrogen chloride gas and calcium chloride in ethanol to provide the compound of Formula-11.

11. The process according to claim 1, further comprising purifying the compound of Formula-11, comprising:

a) dissolving the compound of Formula-11 in alcoholic solvent;
b) adding a non-polar solvent selected from ether solvents, ester solvents, ketone solvents, nitrile solvents, hydrocarbon solvents or chloro solvents to the above obtained solution of step (a);
c) stirring the solution; and
d) filtering the obtained solid and drying to get crystalline form-N of compound of Formula-11.

12. The process according to claim 1, wherein steps (g) and (h) are performed by the steps comprising:
reacting n-hexanol and N,N-carbonyldiimidazole in a chloro solvent to provide the amide compound; and
reacting the amide compound in-situ with the compound of Formula-11 in presence of an inorganic base in a solvent selected from nitrile solvents, polar solvents or its mixture thereof to provide compound of Formula-1.

13. The process according to claim 1, wherein the compound of Formula-10 is a crystalline form-M of compound of Formula-10
which is characterized by:
a) a PXRD pattern having peaks at 4.9, 14.0, 14.6, 16.3, 18.4 and 22.4±0.2 degrees of 2θ;
b) an IR spectrum having absorption peaks at 3345, 2216, 1174 and 1032 cm$^{-1}$; and
c) a DSC thermogram showing an endotherm at 195.24° C.

14. The process according to claim 1, wherein the compound of Formula-11 is a crystalline form-N of compound of Formula-11
which is characterized by:
a) a PXRD pattern having peaks at 3.6, 10.8, 22.9 and 32.6±0.2 degrees of two-theta;
b) an IR spectrum showing absorption peaks at 3155, 1179 and 1044 cm$^{-1}$; and
c) a DSC thermogram showing an endotherm at 199.65° C.

15. The process according to claim 1, wherein the compound of Formula-1 is a Dabigatran etexilate salt selected from:
i. Dabigatran etexilate-(−)-camphor sulfonate salt;
ii. crystalline form-M of Dabigatran etexilate (−)-camphor sulfonate characterized by PXRD pattern having peaks at 4.9, 5.3, 18.6, 6.2, 11.6, 17.3, 18.8 and 20.5±0.2 degrees of 2θ values;
iii. crystalline form-S of Dabigatran etexilate oxalate characterized by PXRD pattern having peaks at 3.9, 7.5, 7.8, 11.9, 18.2, 20.0 and 27.0±0.2 degrees of 2θ values; or
iv. crystalline form-N of Dabigatran etexilate fumarate characterized by PXRD pattern having peaks at 4.9 and 5.2±0.2 degrees of 2θ values.

* * * * *